US012564229B2

(12) United States Patent
Webb

(10) Patent No.: US 12,564,229 B2
(45) Date of Patent: Mar. 3, 2026

(54) MEDICAL HAND COVERING

(71) Applicant: Stethoglove GmbH, Hamburg (DE)

(72) Inventor: Ian Alexander Webb, London (GB)

(73) Assignee: STETHOGLOVE GMBH (DE)

( * ) Notice: Subject to any disclaimer, the term of this patent is extended or adjusted under 35 U.S.C. 154(b) by 829 days.

(21) Appl. No.: 16/941,846

(22) Filed: Jul. 29, 2020

(65) Prior Publication Data

US 2021/0030087 A1 Feb. 4, 2021

Related U.S. Application Data

(60) Provisional application No. 62/881,013, filed on Jul. 31, 2019.

(51) Int. Cl.
A41D 19/01 (2006.01)
A41D 19/00 (2006.01)
(Continued)

(52) U.S. Cl.
CPC ......... A41D 19/01 (2013.01); A41D 19/0006 (2013.01); A41D 19/0055 (2013.01);
(Continued)

(58) Field of Classification Search
CPC ........ A41D 19/00–046; A41D 2300/00; A41D 2300/50; A41D 2500/00; A41D 2500/20;
(Continued)

(56) References Cited

U.S. PATENT DOCUMENTS 3,025,403 A * 3/1962 Belknap .................. G21F 3/035
976/DIG. 339
4,660,228 A * 4/1987 Ogawa .................... B32B 5/022
2/167
(Continued)

FOREIGN PATENT DOCUMENTS

CN 204847566 U 12/2015
CN 205163048 4/2016
(Continued)

OTHER PUBLICATIONS

Extended European Search Report dated Nov. 24, 2020 issued in connection with European Application No. 20188417.8, seven (7) pages.
(Continued)

*Primary Examiner* — Michelle J Lee
(74) *Attorney, Agent, or Firm* — Merek, Blackmon & Voorhees, LLC

(57) ABSTRACT
Disclosed herein is a medical hand covering for tightly enclosing a hand holding a medical instrument to prevent and/or minimize transmission of infectious agents upon examination. The medical hand covering may be prepared by a variety of methods, such as dipping and curing or welding and die cutting. The medical hand covering may have a variety of uses, such as minimizing transmission of infectious agents and reduce anxiety in patients via inclusion of a printed character on the medical hand covering. Also disclosed herein are methods for packaging, devices for dispensing, methods for dispensing, and kits encompassing the medical hand coverings described herein.

14 Claims, 24 Drawing Sheets

(51) Int. Cl.

| | |
|---|---|
| *A61B 7/02* | (2006.01) |
| *A61B 42/10* | (2016.01) |
| *B29C 41/14* | (2006.01) |

(52) U.S. Cl.
CPC ................ *A61B 7/02* (2013.01); *A61B 42/10* (2016.02); *A41D 2300/50* (2013.01); *A41D 2500/20* (2013.01); *A41D 2600/00* (2013.01); *B29C 41/14* (2013.01)

(58) Field of Classification Search
CPC .... A41D 2600/00; A61B 42/00; A61B 42/10; A61B 46/00; A61B 46/10; A61B 46/20–23; A61B 46/27; A61B 7/02–045; B29C 41/02; B29C 41/14
See application file for complete search history.

(56) References Cited

U.S. PATENT DOCUMENTS

| | | | | |
|---|---|---|---|---|
| 5,484,283 | A | * | 1/1996 | Franetzki ............... A61B 1/042 |
| | | | | 433/116 |
| 5,486,322 | A | * | 1/1996 | Fuchs ....................... A61F 6/04 |
| | | | | 264/300 |
| 5,564,431 | A | * | 10/1996 | Seward .................. A61B 50/30 |
| | | | | 600/528 |
| 5,747,751 | A | * | 5/1998 | Weckerle ............... A61B 46/10 |
| | | | | 600/528 |
| 6,578,729 | B2 | * | 6/2003 | Grinberg ............ B65D 83/0894 |
| | | | | 221/26 |
| 7,806,267 | B2 | * | 10/2010 | Pack-Walden ....... B65D 33/002 |
| | | | | 206/390 |
| 10,117,473 | B2 | | 11/2018 | Sullivan et al. |
| 2007/0124849 | A1 | | 6/2007 | Williams et al. |
| 2007/0267026 | A1 | * | 11/2007 | Grant-Jennings ...... A61B 46/10 |
| | | | | 128/846 |
| 2009/0020357 | A1 | | 1/2009 | Pack-Walden et al. |
| 2009/0158499 | A1 | | 6/2009 | Singer |
| 2010/0326850 | A1 | | 12/2010 | Manlpaz |
| 2011/0010822 | A1 | | 1/2011 | Singer |
| 2015/0257834 | A1 | | 9/2015 | Mirkarimi |
| 2017/0095017 | A1 | | 4/2017 | Mirkarimi |

FOREIGN PATENT DOCUMENTS

| | | | | |
|---|---|---|---|---|
| CN | 108623864 | A | | 10/2018 |
| CN | 109788812 | A | | 5/2019 |
| CN | 208876580 | | | 5/2019 |
| CN | 208876580 | U | * | 5/2019 |
| WO | WO2017205357 | | | 11/2017 |
| WO | WO2018/191639 | | | 10/2018 |

OTHER PUBLICATIONS

Machine generated translation of CN208876580.
Office Action issued in connection with Chinese Patent Application No. 202010747836.3 dated Feb. 27, 2024.
Office Action issued in connection with Taiwanese Patent Application No. 109126036.
Office Action issued in connection with Singaporean Patent Application No. 10202007300U dated May 30, 2024.
Office Action issued in connection with Chinese Patent Application No. 202010747836.3 dated Jan. 14, 2025.
Machine translation of Office Action issued in connection with Chinese Patent Application No. 202010747836.3 dated Jan. 14, 2025.
Office Action issued in connection with Chinese Patent Application No. 202010747836.3 dated Sep. 4, 2024.
Machine translation of Office Action issued in connection with Chinese Patent Application No. 202010747836.3 dated Sep. 4, 2024.
Canadian Office Action dated Aug. 5, 2025 issued in connection with Canadian Patent Application No. 3,088, 121, sixteen (16) pages.
Office Action dated Nov. 13, 2025 issued in India Patent Application No. 202014032518, seven (7) pages.

\* cited by examiner

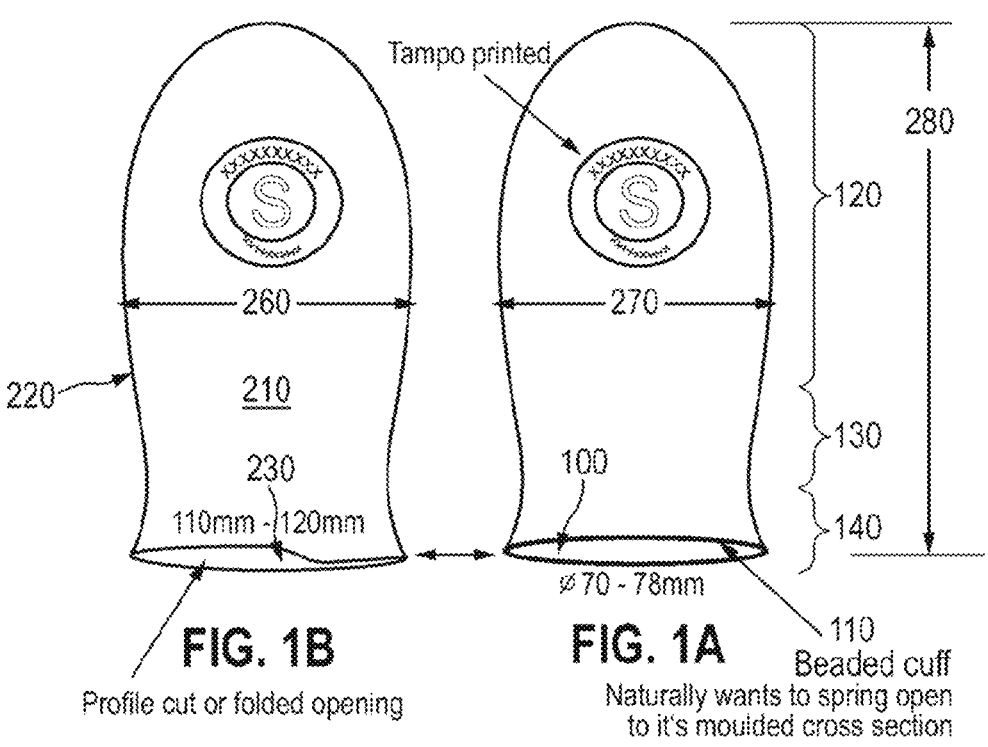
FIG. 1B
Profile cut or folded opening
FIG. 1A
Beaded cuff
Naturally wants to spring open
to it's moulded cross section
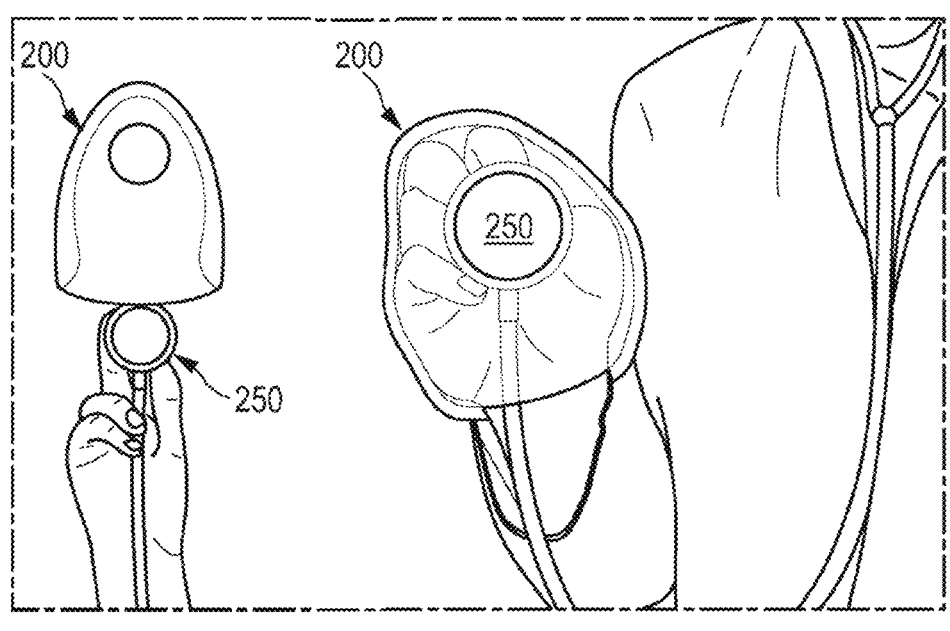
FIG. 2

Ceramic or Aluminum moulds are dipped into liquid rubber

The rubber coats the mould and is then heat cured. The moulds are rotated and then inverted When cured the rubber can be tampo (pad) printed with graphics. The extra material around the cuff is then rolled into a bead The final product is removed from the mould by air or by hand and collated into boxes. The eliptical cross section will allow covering to be stacked

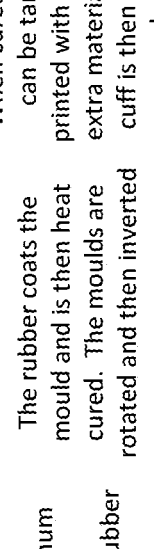
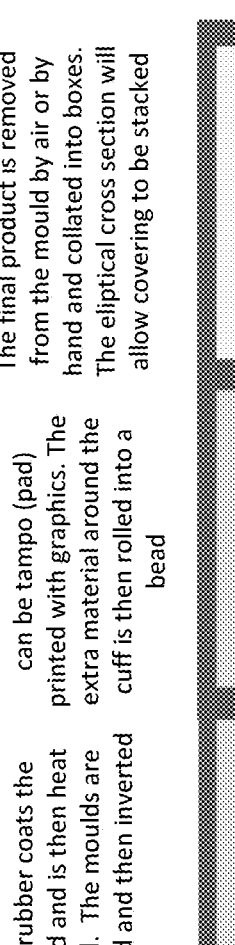
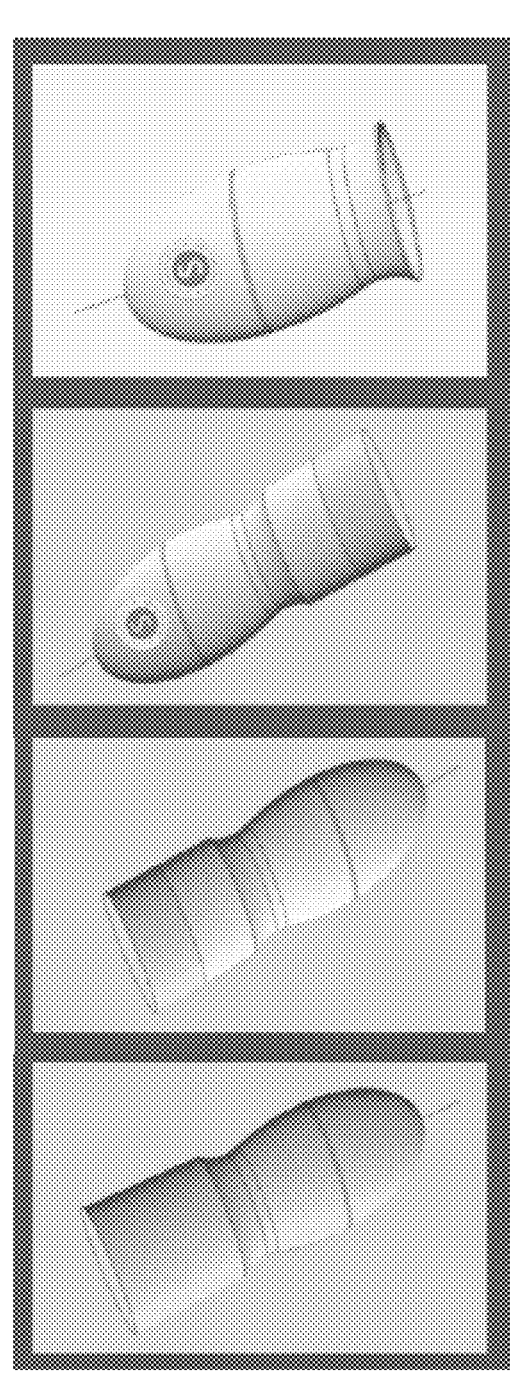

FIG. 4A          FIG. 4B          FIG. 4C          FIG. 4D

540
Waste web material is stripped away and recycled

Products are collated into stacks or frangibly connected to be rolled up or sealed in cartons 530
Rotary or reciprocating tools heat weld the 2 materials together and also profile cut the covering shape 2 reels of pain and pre-printed materials are brought together for welding & cutting

520

510

| MATERIAL | CETTE CELL OPEN | 24 HOUR DISCHARGE V | PERCENTAGE DIFFERENCE IN OPEN |
|---|---|---|---|
| A. CONTROL NO COVERING | 334.135 V | | N/A |
| D. Thermoplastic Polyurethane e.g. Stethoglove | 328.170 V | | 1.79% |
| C. Vinyl | 318.979 V | | 4.83% |
| F. Polyisoprene | 310.762 V | | 7.01% |
| E. Polyethylene e.g. Stethoguard | 238.872 V | | 28.4% |
| B - Spun Woven PE e.g. Stethoscap | 235.103 V | | 29.64% |

Fig. 12

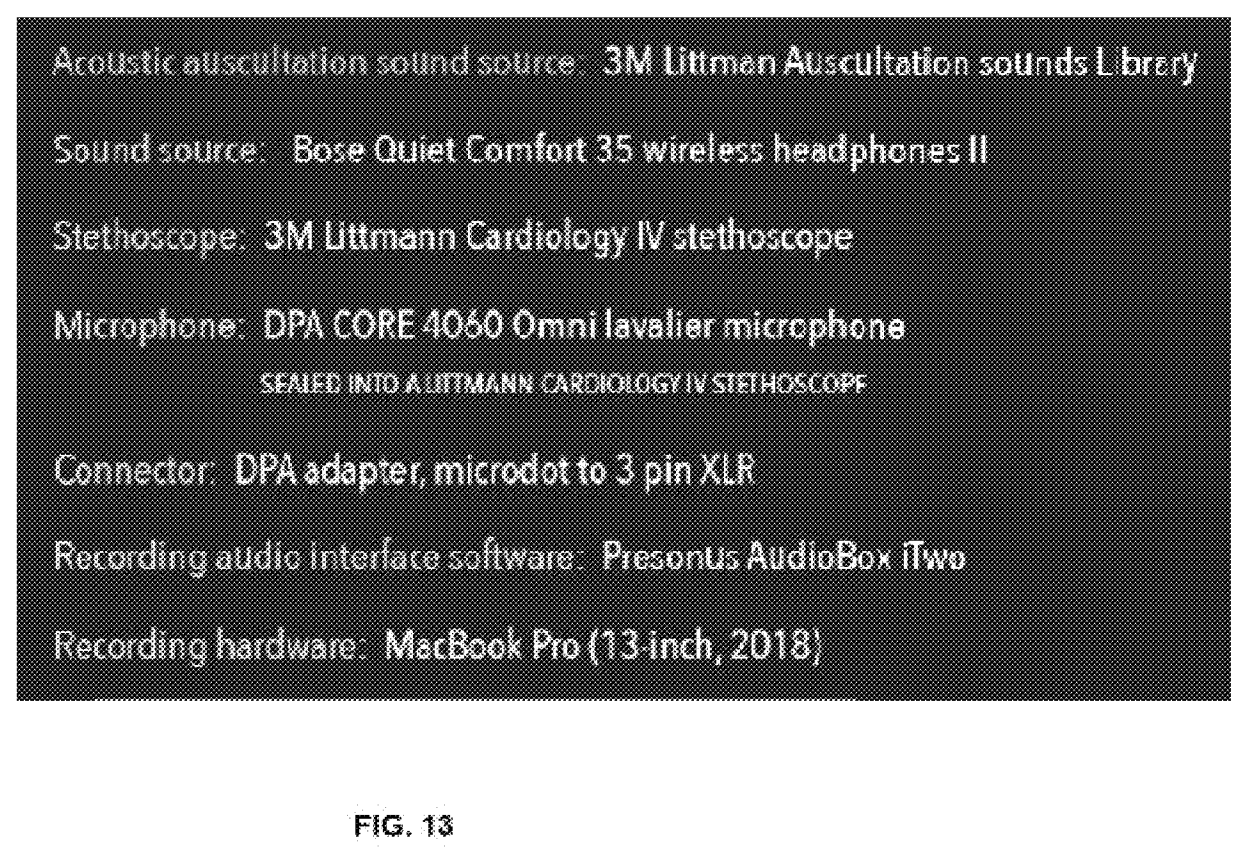

Acoustic auscultation sound source: 3M Littman Auscultation sounds Library

Sound source: Bose Quiet Comfort 35 wireless headphones II

Stethoscope: 3M Littman Cardiology IV stethoscope

Microphone: DPA CORE 4060 Omni lavalier microphone
SEALED INTO A LITTMAN CARDIOLOGY IV STETHOSCOPE Connector: DPA adapter, microdot to 3 pin XLR Recording audio interface software: Presonus AudioBox iTwo Recording hardware: MacBook Pro (13 inch, 2018)

FIG. 13

MEDICAL HAND COVERING

FIELD OF THE INVENTION

The present invention relates to a medical hand covering for enclosing a hand holding a medical instrument to prevent and/or minimize transmission of infectious agents upon examination, methods of its preparation, methods of its use, methods of its packaging, devices for dispensing such coverings, methods of dispensing, and kits thereof.

BACKGROUND OF THE INVENTION

In the medical field, transmission of infectious agents and other contaminants is an ongoing concern. To address the spread of infectious diseases in health care settings, the use of protective covers, such as, gloves, masks, gowns, and protective eyewear, is urged. Many of the precautionary measures that are presently in place protect against the spread of infectious agents from the health care worker to the patient and vice versa. Despite these measures, infectious agents may still get transmitted from health care workers to patients through medical instruments utilized for examining the patients (e.g., stethoscopes). While there are some recommendations for sterilizing medical instruments between each patient examination, such practices are not strictly enforced.

There remains a need for a medical covering that is effective, convenient to use, and easy to apply so that it will gain acceptance among health care workers.

OBJECTS AND SUMMARY OF THE INVENTION

It is an object of the present invention to provide a medical hand covering that is sufficiently soft, stretchy, and conformable to tightly enclose a hand holding a medical instrument.

It is another object of the present invention to minimize transmission of infectious agents to a patient being examined.

It is a further object of the present invention to reduce anxiety in patients being examined with a medical instrument.

The above objects and others are met by the instant disclosure, which in some embodiments is directed to a medical hand covering comprising one or more materials defining an inner cavity adapted to tightly enclose an adult hand holding a medical instrument. The medical hand covering may further comprise an opening on one end of the covering adapted to allow entry of the hand and the medical instrument into the inner cavity. The one or more materials, independently, may comprise one or more of thermoset rubbers (such as latex, nitrile, silicon, polyisoprene, neoprene), all thermoplastic materials, such as thermoplastic urethane (TPU), vinyl, low density polyethylene, spun woven polyethylene (spun woven PE), or ethylene and vinyl acetate (EVA). The one or more materials may comprise a thermoset rubber. The material thickness may be about 40 to about 125 μm, typical about 60 μm. The hardness may be about 30 to about 80 Shore A. The elongation at break, DIN EN ISO 527 may be >600%. The tear propagation resistance KN/m when using 60 μm material on the basis of DIN ISO 34-1,B may be >40. The one or more materials may comprise thermoplastic materials, preferably made by welding profiling and cutting. Such thermoplastic materials may have a material thickness of about 30 to 100 μm, preferably about 50 μm. The hardness may be about 40 to about 100 Shore A. The elongation at break, DIN EN ISO 527, may be >400%. The tear propagation resistance KN/m using 50 μm material, on the basis of DIN ISO 34-1,B, may be >40. Such thermoplastic materials have a high slip factor to reduce 'sticking' during donning procedure. The one or more materials may comprise water soluble Poly Vinyl Alcohol (PVOH). The one or more materials may comprise bio based materials to improve eco credits and performance. All afore-mentioned examples of thermosetting rubbers and thermoplastic materials are easier to clean/sterilise in-line using far-UVC at about 222 Nm. All afore-mentioned examples of thermosetting rubbers and thermoplastic materials are more transparent than thermosetting rubbers and thermoplastic materials not falling under the afore-mentioned examples. All afore-mentioned examples of thermosetting rubbers and thermoplastic materials show good UV stability, hydrolysis resistance and microbial resistance. In case it is desired to produce the afore-mentioned examples of thermosetting rubbers and thermoplastic materials at high speeds, it is preferred to provide a sacrificial PE carrier film to reduce stretch during such manufacturing. Particularly preferred materials for the one or more materials defining the inner cavity of the medical hand covering comprise thermoplastic polyurethane (TPU Polyether variant), Polyisoprene rubber, and/or vinyl, since all these materials have soft, stretchy, hypoallergenic, tear resistant, bacteria barrier, and translucent qualities at the same time so that there are in particular at the same time stretchy and acoustically transmissive. The one or more materials may be acoustically transmissive, in particular acoustically transmissive with respect to the acoustic performance of a stethoscope, being the medical instrument, preferably in that a sound curve of a bare stethoscope compared to the stethoscope enclosed in the medical hand covering are nearly completely superimposed in a medically important frequency range of about 50 Hz to about 2 kHz, wherein nearly completely superimposed means that there is less than about 30% decibel reduction, or less than about 25% decibel reduction, or less than about 20% decibel reduction, or less than about 15% decibel reduction, or less than about 10% decibel reduction, or less than about 8% decibel reduction, or less than about 5% decibel reduction, or less than about 3% decibel reduction, or less than about 1% decibel reduction, or less than about 0.5% decibel reduction, or substantially no decibel reduction, based on the decibel value of the bare stethoscope at said medical important frequency range. The one or more materials may be stretchy, in particular the medical hand covering may has a cross-section that is round or oval, and preferably the unstretched circumference around the medical hand covering, measured across the side of a palm to a thumb of the adult human hand, ranges from about 200 mm to about 260 mm, or from about 210 mm to about 250 mm, or from about 220 mm to about 240 mm, and when the medical hand covering preferably is two-sided and lays flat, each face preferably having a width ranging from about 100 mm to about 150 mm, or from about 105 mm to about 125 mm, or from about 110 mm to about 120 mm, and when the medical hand covering is oval, a cross section, minor axis plus major axis, preferably ranges from about 100 mm to about 130 mm, or from about 105 mm to about 125 mm, or from about 110 mm to about 120 mm, and when the medical hand covering is three dimensional, preferably when it has been removed from a mould after having been prepared by mould dipping and curing, a cylinder cross section preferably ranges from about 65 mm to about 85 mm, or from about 68 mm to about 82 mm, or from about 70 mm to about 78 mm, and preferably a stretched circumference is about 2, or about 3, or about 4, or about 5, or about 6, or about 7, or about 8, or about 9, or about 10, or about 11, or about 12, or about 13, or about 14, or about 15 fold greater than an un-stretched circumference. The medical hand covering may be prepared by a process of dipping and curing. The medical hand covering may be ambidextrous. The inner cavity may be fingerless. The inner cavity may comprise a separate inner cavity for separating the thumb of the hand. The medical instrument may be a stethoscope. A sound quality obtained via the stethoscope when it is used with the medical hand covering may be substantially the same as a sound quality obtained via the stethoscope when it is used without the medical hand covering. The sound quality may comprise one or more of amplitude, frequency, or decibel level. The opening further may comprise a cuff bead.

In some embodiments, the instant disclosure is directed to a medical hand covering comprising a first surface corresponding to a palm side of an adult human and a second surface corresponding to a dorsal side of an adult human hand. The first and the second surface may define an inner cavity adapted to tightly enclose a hand holding a medical instrument. The medical hand covering may further comprise an opening on one end of the medical hand covering to allow entry of the hand and the medical instrument into the inner cavity. The first surface may comprise a first material and the second surface comprises a second material. The first material may be different from the second material. The first material may be the same as the second material. The first material and the second material, independently, may comprise one or more of thermoset rubbers (such as latex, nitrile, silicon, polyisoprene, neoprene), all thermoplastic materials, such as thermoplastic urethane (TPU), vinyl, low density polyethylene, spun woven PE, or ethylene and vinyl acetate (EVA). The first surface may comprise thermoplastic urethane. The second surface may comprise vinyl or low density polyethylene or spun woven PE. The first surface may be transparent or opaque. The first surface may comprise a material that is acoustically transmissive. The first surface may comprise a material that is stretchy. The first surface and/or the second surface may comprise a printed character. The first surface and the second surface may be heat welded and die cut. The medical hand covering may be ambidextrous. The inner cavity may be fingerless. The inner cavity may comprise a separate inner cavity for separating the thumb of the hand. The medical instrument may be a stethoscope. A sound quality obtained via the stethoscope when it is used with the medical hand covering may be substantially the same as a sound quality obtained via the stethoscope when it is used without the medical hand covering. The sound quality may comprise one or more of amplitude, frequency, decibel level. The first surface and the second surface may be seamless. The inner cavity may be adapted to tightly enclose the hand holding the medical instrument in a fisted position. The inner cavity may be adapted to tightly enclose both the hand holding the medical instrument and at least a part of the medical instrument gripped by the hand, the part being for example a chestpiece of a stethoscope in case the medical instrument is a stethoscope.

In some embodiments, the instant disclosure is directed to a method for protecting a patient from transmission of infectious agents. The method may comprise holding a medical instrument in a hand and inserting the hand holding the medical instrument into a medical hand covering in accordance with embodiments described herein. The medical hand covering may comprise (A) or (B), wherein (A)

may comprise: a first surface corresponding to a palm side of the hand; a second surface corresponding to a dorsal side of the hand; the first and second surface defining an inner cavity adapted to tightly enclose the hand holding the medical instrument; and an opening on one end of the covering adapted to allow entry of the hand and medical instrument into the inner cavity; and wherein (B) may comprise: one or more materials defining an inner cavity adapted to tightly enclose an adult hand holding a medical instrument; and an opening on one end of the covering adapted to allow entry of the hand and medical instrument into the inner cavity. Less infectious agents may be transmitted to a surface contacted with the hand holding the medical instrument enclosed in the medical hand covering as compared to a surface contacted with the hand holding the medical instrument without being enclosed in the medical hand covering.

In some embodiments, the instant disclosure is directed to a method for reducing anxiety in a patient upon examination with a medical instrument. The method may comprise examining the patient with a medical hand covering enclosing a hand holding a medical instrument. The medical hand covering may be any of the ones described herein that include a printed character thereon. The medical hand covering may comprise (A) or (B), wherein (A) may comprise: a first surface corresponding to a palm side of the hand; a second surface corresponding to a dorsal side of the hand; the first and second surface defining an inner cavity adapted to tightly enclose the hand holding a medical instrument; and an opening on one end of the covering adapted to allow entry of the hand and medical instrument into the inner cavity, and wherein the first surface and/or the second surface may comprise a printed character; and wherein (B) may comprise: one or more materials defining an inner cavity adapted to tightly enclose an adult hand holding a medical instrument; an opening on one end of the covering adapted to allow entry of the hand and medical instrument into the inner cavity, and wherein a character may be printed on the one or more materials. A patient examined with the hand holding the medical instrument enclosed in the medical hand covering may experience less anxiety as compared to a patient examined with a hand holding the medical instrument without being enclosed in the medical hand covering.

In some embodiments, the instant disclosure is directed to a method for manufacturing a medical hand covering. In one embodiment, the method may comprise dipping a mould into the one or more materials that are in a liquid form, and curing the one or more materials coated on the dipped mould to form the medical hand covering. The method may comprise rotating the dipped mould. The method may comprise inverting the dipped mould. The method may comprise printing a character, a logo, a graphic, or combinations thereof on the medical hand covering. The method may comprise rolling excess of the one or more materials at the opening of the medical hand covering into a rolled cuff bead. The method of may comprise a ceramic and/or aluminum. In another embodiment, the method may comprise welding a seam between a first surface corresponding to a palm side of an adult human hand, and a second surface corresponding to a dorsal side of the hand, and die cutting the welded seam to form the medical hand covering. The method may comprise that the first surface and/or the second surface are formed from a first film of the one or more materials and/or a second film of the one or more materials, respectively. The first film and/or the second film may comprise a pre-printed character, logo, graphic, or combinations thereof.

In some embodiments, the instant disclosure is directed to a medical hand covering dispensing device. The dispensing device may comprise a container defining an interior for storing one or more medical hand coverings and an aperture through which medical hand coverings within the container may be removed. The stack of medical hand coverings may be connected in a daisy chain configuration. The stack of medical hand coverings may be stored in the interior of the container such that a surface of the medical hand covering corresponding to a dorsal side of a hand enclosed by the medical hand covering faces outwards of the container. The stack of medical hand coverings may be stored in the interior of the container such that the one end of the medical hand covering closer to the opening faces outwards of the container.

In some embodiments, the instant disclosure is directed to a kit comprising one or more of a stack of medical hand coverings, a dispensing device, and a medical instrument, e.g. a stethoscope.

In some embodiments, the instant disclosure is directed to a method for packaging a plurality of medical hand coverings. The method may comprise stacking the plurality of medical hand coverings in a container; rolling the plurality of medical hand coverings on a roll, a spool, or a drum; connecting the plurality of medical hand coverings in a daisy chain configuration, or a combination thereof. The method may comprise flattening the plurality of medical hand coverings and filling into a container. The method may comprise sterilizing the medical hand covering. The sterilizing may comprise UV sterilizing, Gamma irradiating, ethylene oxide sterilizing (ETO), or combinations thereof.

In some embodiments, the instant disclosure is directed to a method of dispensing a medical hand covering from a dispensing device. The method may comprise removing a medical hand covering from the container via a surface of the medical hand covering corresponding to a dorsal side of a hand enclosed by the medical hand covering or via a one end of the medical hand covering closer to the opening so as not to compromise the sterility of a surface of the medical hand covering corresponding to a palm side of a hand enclosed by the medical hand covering.

Definitions

As used herein, the singular forms "a," "an," and "the" include plural references unless the context clearly indicates otherwise. Thus, for example, reference to "a material" includes a single material as well as a mixture of two or more different materials; and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, a "patient" refers to a subject, particularly a human (but could also encompass a non-human), who has presented a clinical manifestation of a particular symptom or symptoms suggesting the need for treatment, who is treated prophylactically for a condition, or who has been diagnosed with a condition to be treated.

The term "subject" encompasses the definition of the term "patient" and does not exclude individuals who are otherwise healthy.

The terms "treatment of" and "treating" include the administration of an active agent(s) with the intent to lessen the severity of or prevent a condition, e.g., delayed graft function.

The terms "prevention of" and "preventing" include the avoidance of the onset of a condition, e.g., delayed graft function.

The term "condition" or "conditions" refers to those medical conditions, such as anxiety or infection, that can be treated, mitigated or prevented by administration to a subject of an effective amount of an active agent or by taking precautionary measures (such as utilizing a sanitary medical covering for a medical instrument).

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

BRIEF DESCRIPTION OF THE DRAWINGS

The above and other features of the present disclosure, their nature, and various advantages will become more apparent upon consideration of the following detailed description, taken in conjunction with the accompanying drawings, in which:

FIG. 1A depicts a medical hand covering prepared by mould dipping and curing according to an embodiment.

FIG. 1B depicts a medical hand covering prepared by welding and die cutting according to an embodiment.

FIG. 2 depicts a medical hand covering, according to an embodiment, tightly enclosing a hand holding a stethoscope.

FIG. 4A-4D depict a mould dipping and curing process for manufacturing a medical hand covering according to an embodiment.

FIG. 12 shows the summary of the testings of FIGS. 10A-10F using source 2, i.e. the heart sound of a heart with severe arortic stenosis.

FIG. 13 shows the test equipment used for all testings shown in FIGS. 8-12. Unless not indicated otherwise all testings in the present patent application have been conducted at room temperature of about 23 degree Celsius and under normal atmospheric pressure of about 1013.25 millibar.

DETAILED DESCRIPTION

Figure 3:
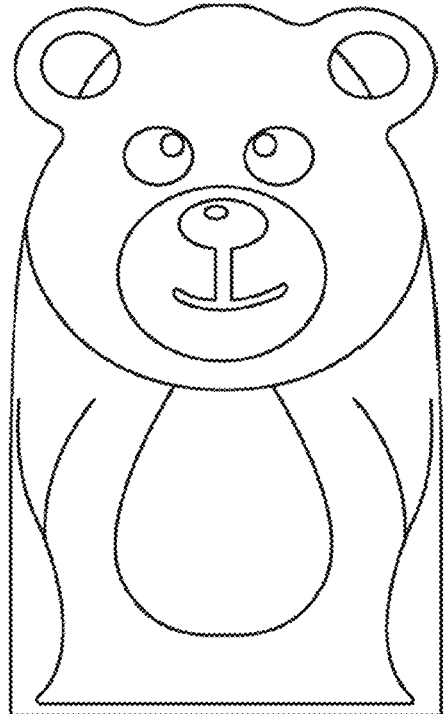
FIG. 3 depicts a medical hand covering with a character printed thereon, according to an embodiment.

The present invention is directed to a medical hand covering adapted to tightly enclose a hand holding a medical instrument (i.e. enclose both—the hand and the medical instrument—as the hand holds the medical instrument), methods of preparation thereof, methods of packaging thereof, methods of dispensing thereof, packaging and/or dispensing containers enclosing medical hand coverings, methods of using the medical hand coverings, and kits comprising the medical hand coverings.

Medical Hand Covering

In one embodiment, the instant disclosure encompasses a medical hand covering comprising one or more materials defining an inner cavity adapted to tightly enclose an adult hand holding a medical instrument as shown in FIG. 1A. The medical hand covering may further comprise an opening 100 on one end of the covering adapted to allow entry of the hand and medical instrument into the inner cavity. The medical hand covering according to this embodiment may further comprise a cuff bead 110 around the opening. Medical hand coverings according to this embodiment may be prepared by a process of dipping and curing, as described in further detail below with respect to FIGS. 4A-4D.

Medical hand coverings as shown in FIG. 1A may have an hourglass shape characterized by a wider width in the inner cavity portion that is to enclose the hand holding the medical instrument (section 120), a narrower width closer to the one end by the opening (section 130), and again a wider width at the very end of the medical hand covering where the opening is (section 140).

In another embodiment, the instant disclosure encompasses a medical hand covering comprising a first surface

210 corresponding to a palm side of an adult human hand, and a second surface 220 corresponding to a dorsal side of an adult human hand, as shown in FIG. 1B. The first and second surface may define an inner cavity adapted to tightly enclose the hand holding a medical instrument. The medical hand covering may further comprise an opening 230 on one end of the covering adapted to allow entry of the hand and medical instrument into the inner cavity. Medical hand coverings according to this embodiment may be prepared by heat welding and die cutting, as described in further detail below with respect to FIG. 5. The transition between the first surface and the second surface may be seamless.

In certain embodiments, the first surface 210 may comprise a first material and the second surface 220 may comprise a second material. The first material and the second material may be the same or different. For instance, the first surface may comprise thermoplastic urethane and/or the second surface may comprise vinyl or low density polyethylene.

The materials forming the medical hand covering may, independently, comprise one or more of thermoset rubbers (such as latex, nitrile, silicon, polyisoprene, neoprene, polychloroprene), all thermoplastic materials (such as polyurethane (TPU), vinyl, low density polyethylene, spun woven PE, or ethylene and vinyl acetate (EVA)). Thermoset rubbers may be particularly suitable for medical hand coverings manufactured by a dipping and curing method. Thermoplastic materials may be particularly suitable for medical hand coverings manufactured by a welding and die cutting method. In some embodiments, the materials used for the medical hand coverings described herein may be warm to touch and patient friendly.

Different consideration may determine the material(s) ultimately selected for the medical hand covering, including, but not limited to, elasticity, hardness, tactile sensitivity, dexterity, acoustic transmissivness, consumer needs (e.g., accounting for allergies such as latex allergies which effect about 6.4% of the general population), color, opacity, thickness, ease to process, stability, and the like.

Suitable thermoplastic materials may have a hardness ranging from about 20 Shore A to about 100 Shore A, from about 30 Shore A to about 90 Shore A, or from about 40 Shore A to about 85 Shore A. The thickness for medical hand coverings comprising a thermoplastic material may range from about 5 microns to about 150 microns, from about 15 microns to about 135 microns, or from about 25 microns to about 125 microns.

Suitable thermoset rubbers may have a hardness ranging from about 10 Shore A to about 90 Shore A, from about 20 Shore A to about 75 Shore A, or from about 30 Shore A to about 60 Shore A. The thickness for medical hand coverings comprising a thermoset rubber may range from about 20 microns to about 200 microns, from about 35 microns to about 175 microns, or from about 50 microns to about 150 microns.

Medical instruments that may be used with the medical hand covering described herein include, without limitations, stethoscope, ultrasound probe, acoustic probe, hydro distention probe, near infra-red probe, and the like. Other medical instruments that require minimal diminishing of their performance (e.g., less than about 10%, less than about 8%, less than about 5%, less than about 4%, less than about 3%, less than about 2%, or less than about 1% diminishing in their performance) may be used with the medical hand covering described herein.

It is vital that the medical hand covering be made sufficiently soft and conformable so that it is able to stretch over both—the medical instrument and the hand holding the medical instrument. For instance, as shown in FIG. 2, when the medical instrument is a stethoscope, the medical hand covering 200 should stretch over the stethoscope head 250 without restricting rotation of the stethoscope head for easy positioning of the stethoscope head on the patient (via the medical hand covering). The medical hand covering is designed to enable a physician to hold the medical instrument (e.g., a stethoscope) in a way that is natural for the physician. In some embodiments, the medical hand covering may be designed to accommodate a physician holding a medical instrument, such as a stethoscope, in a fisted position, with a finger gripped around the chestpiece, with the first and second finger in a position similar to holding a cigar, between two fingers, or a combination thereof.

When the medical instrument is a stethoscope or another medical instrument that is used by examining sound waves, it is important that the medical hand covering be made of a material that is acoustically transmissive so as to not impair sound transmission. The phrase "acoustically transmissive," as used herein, refers to a material through which the transmission of sound is not impaired or only minimally impaired, as may be measured experimentally and quantified based on acoustical impedance, frequency, amplitude, decibel level, or a combination thereof. In some embodiments, the medical hand covering does not alter sound transduction in the medically and diagnostically important frequency spectrum as further exemplified in FIG. 6.

For a similar reason, it is important that the medical hand covering be made of a stretchy material that tightly encloses the hand holding the medical instrument and allows fitting hands and/or instruments of various sizes. A loose fit could generate disruptive background noise. The stretchy material may stretch with some pressure over the medical instrument to create an airtight seal. In some embodiments, the medical hand covering may conform to the medical instrument (e.g., conform to a stethoscope diaphragm and possibly touch the diaphragm when pressed against a patient's skin). The tight seal may allow movement of the medical instrument without generation of additional background sounds (such as crackles) that may lead to a potential misdiagnosis (being that in some instances crackles may be an indicator of a medical problem).

Certain embodiments of the instant disclosure aim at a medical hand covering in which a sound quality obtained via the stethoscope when it is used with the medical hand covering is substantially the same as a sound quality obtained via the stethoscope when it is used without the medical hand covering. The sound quality may be a measure of one or more of amplitude, frequency, or decibel level. For instance, the amplitude and/or frequency and/or decibel level of a sound obtained via the stethoscope when it is used with the medical hand covering may be within about 30%, within about 25%, within about 20%, within about 15%, within about 10%, within about 5%, within about 1%, substantially the same, or the same as the amplitude and/or frequency and/or decibel level of a sound obtained via the stethoscope when it is used without the medical hand covering.

The inner cavity in the medical hand covering may be fingerless or may comprise a separate inner cavity for the thumb of the hand and may be adapted to tightly enclose the hand holding the medical instrument (e.g., adapted to enclose the hand holding the medical instrument in a fisted position). In one embodiment, the medical hand covering is ambidextrous.

In some embodiments, the surface of the medical hand covering corresponding to the palm side of the hand is transparent or opaque. In certain embodiments, the medical hand covering may also have a printed character (as depicted in FIG. 3) on either the surface corresponding to the palm side of the hand or to the dorsal side of the hand.

The medical hand coverings may have a cross-section that is round or oval. The unstretched circumference around the medical hand covering (measured across the side of the palm to the thumb) may range from about 200 mm to about 260 mm, from about 210 mm to about 250 mm, or from about 220 mm to about 240 mm. When the medical hand covering is two-sided and lays flat, each face may have a width 260 ranging from about 100 mm to about 150 mm, from about 105 mm to about 125 mm, or from about 110 mm to about 120 mm. In embodiments where the medical hand covering is oval, the cross section (minor axis plus major axis) ranges from about 100 mm to about 130 mm, from about 105 mm to about 125 mm, or from about 110 mm to about 120 mm. In embodiments where the medical hand covering is three dimensional (i.e., when it is removed from a mould after having been prepared by mould dipping and curing) the cylinder cross section 270 ranges from about 65 mm to about 85 mm, from about 68 mm to about 82 mm, or from about 70 mm to about 78 mm. The stretched circumference may be about 2, about 3, about 4, about 5, about 6, about 7, about 8, about 9, about 10, about 11, about 12, about 13, about 14, or about 15 fold greater than the un-stretched circumference.

The length 280 of the medical hand covering may range from about 100 mm to about 600 mm, from about 150 mm to about 550 mm, from about 200 mm to about 500 mm, from about 220 mm to about 480 mm, from about 220 mm to about 240 mm, from about 240 mm to about 480 mm, from about 300 mm to about 480 mm, from about 350 mm to about 480 mm, or from about 400 mm to about 480 mm long. Longer lengths for the medical hand covering may be designed for sterile applications and the like.

Manufacturing Methods

In one embodiment, the instant disclosure is directed to a method of preparing the medical hand covering by dipping a ceramic or an aluminum mould into one or more materials that are in a liquid form as per FIG. 4A. The method may further comprise curing the one or more materials coating the dipped mould as per FIG. 4B. The method may further comprise rotating the dipped mould and/or inverting the dipped mould. After the one or more materials has been cured, it may be tampo (pad) printed with graphics as per FIG. 4C. Thus, the method may further comprise printing a character, a logo, a graphic, or combinations thereof on the medical hand covering.

The medical hand covering prepared according to this embodiment may comprise one or more materials defining an inner cavity adapted to tightly enclose an adult hand holding a medical instrument. The medical hand covering may further comprise an opening on one end of the covering adapted to allow entry of the hand and medical instrument into the inner cavity. Extra material by the opening end of the medical hand covering may be rolled into a cuff bead around the opening. The rolled bead cuff may have a natural predisposition to spring into round or oval (as moulded), which could make it convenient to grab, prise open the glove, and insert the hand and/or the medical instrument.

The final medical hand covering may be removed from the mould by air or by hand as per FIG. 4D. Medical hand coverings prepared according to the mould dipping and curing process may be three dimensional and may be flattened after removal from the mould, optionally stacked, and packaged (i.e., filled into a container).

In another embodiment, the instant disclosure is directed to a method of preparing the medical hand covering by welding a seam between a first material and a second material and die cutting the medical hand covering shape. The first and second materials may originate from two reels of a first and a second plain or pre-printed film, e.g., 510 and 520 in FIG. 5. For example, the film(s) may be pre-printed with a character, a logo, a graphic, or a combination thereof. The first material may form the first surface corresponding to a palm side of a hand. The second material may form the second surface corresponding to a dorsal side of a hand.

Figure 5:
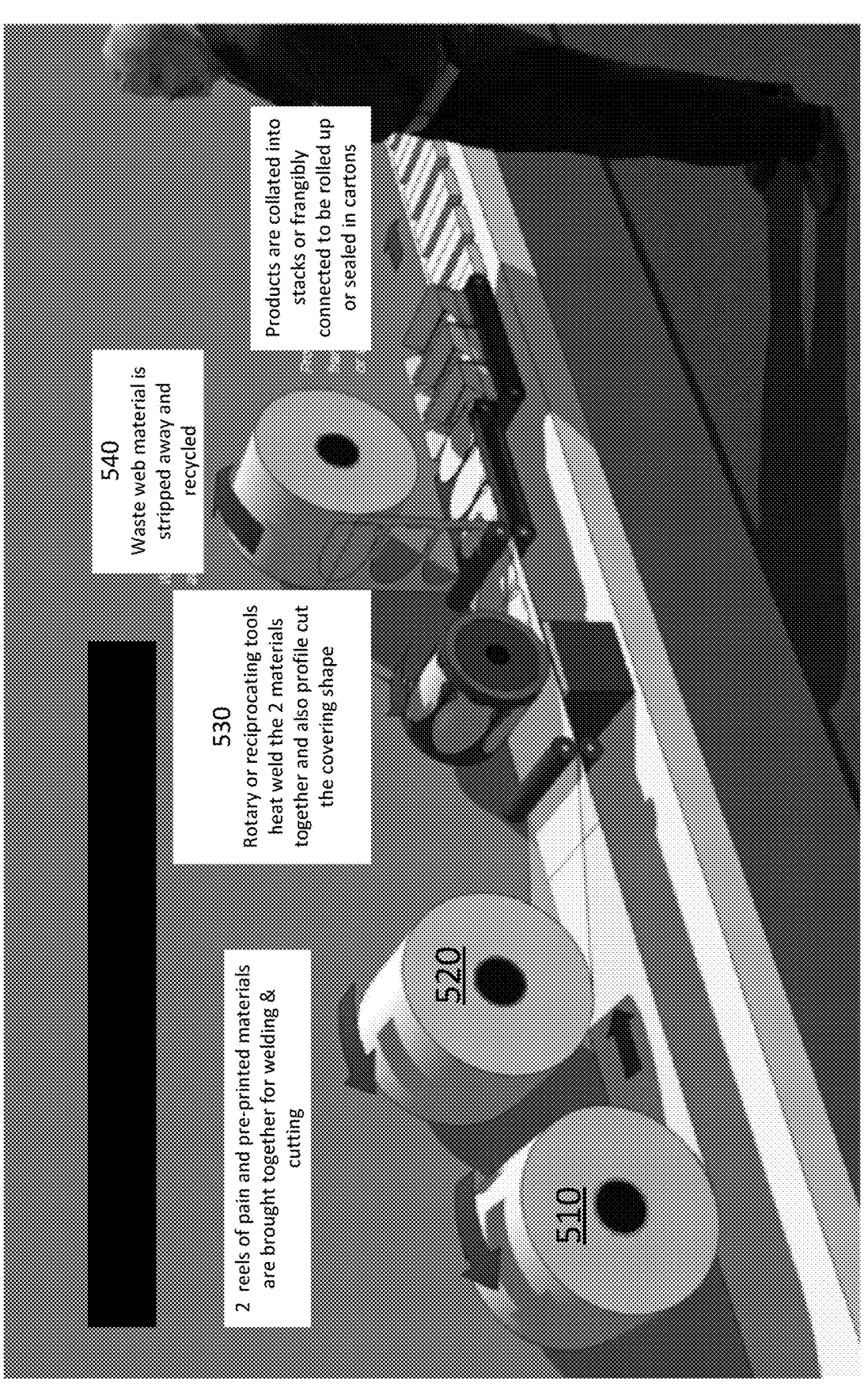
FIG. 5 depicts a welding and dies curring process for manufacturing a medical hand covering according to an embodiment.

Rotary and reciprocating tools may be used to weld the films of the first and second materials together and to profile cut the medical hand covering shape as per part 530 in the process depicted in FIG. 5. The first and the second materials may be welded together by heat welding, RF welding, or ultrasonic welding. It will be appreciated by one of ordinary skill in the art that various suitable tools may be used.

In some embodiments, waste film material that is left over after the shape of the medical hand covering is cut may be stripped away and recycled, as per part 540 in the process depicted in FIG. 5.

Medical hand coverings produced by the heat welding and die cutting manufacturing method may be flat, making them suitable for orderly stacking a plurality of the medical hand coverings in a packaging container or rolling a plurality of medical hand coverings on a roll, a spool, a drum, and the like. In some embodiments, a plurality of medical hand coverings may be connected in a daisy chain configuration prior to packaging.

In certain embodiments, manufacturing and/or packaging methods described herein may further comprise sterilizing the medical hand covering prior to packaging. Various sterilization methods may be utilized, such as, without limitations, UV sterilizing, gamma irradiating, ethylene oxide sterilizing (ETC)), or a combination thereof.

Packaging and Dispensing Devices

Figure 14A:
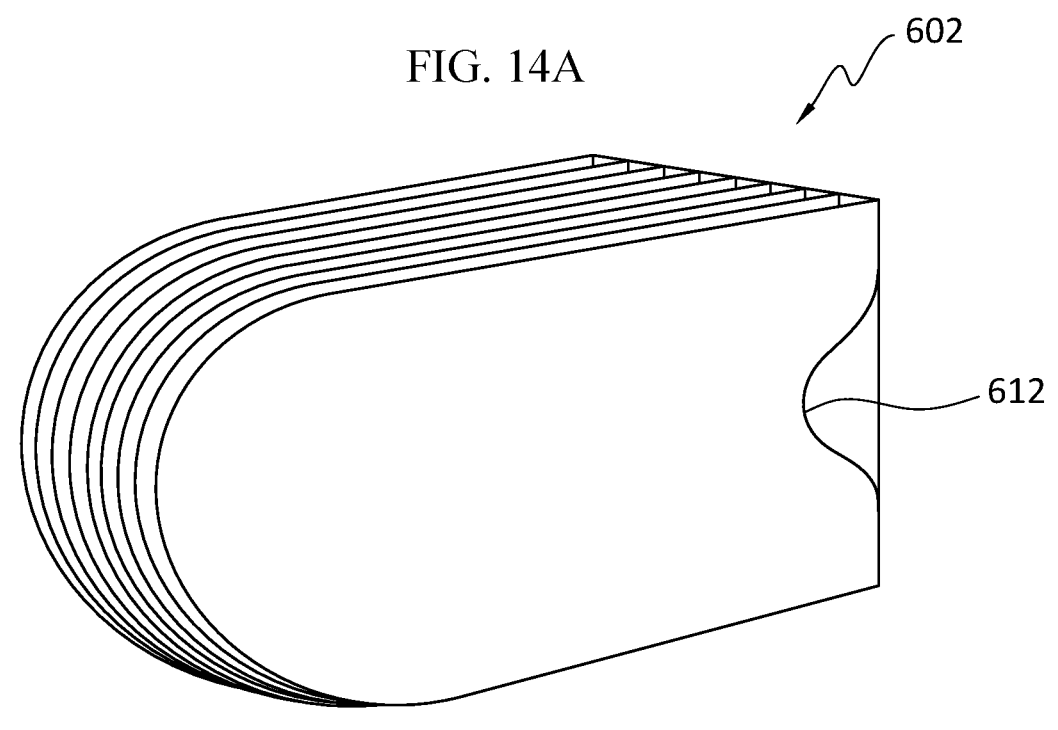
FIG. 14A is a perspective view of a stack of medical hand coverings and FIG. 14B is a perspective view of a medical hand covering dispensing device with a lid or cover in an open position exposing a stack of medical hand coverings.
Figure 14B:
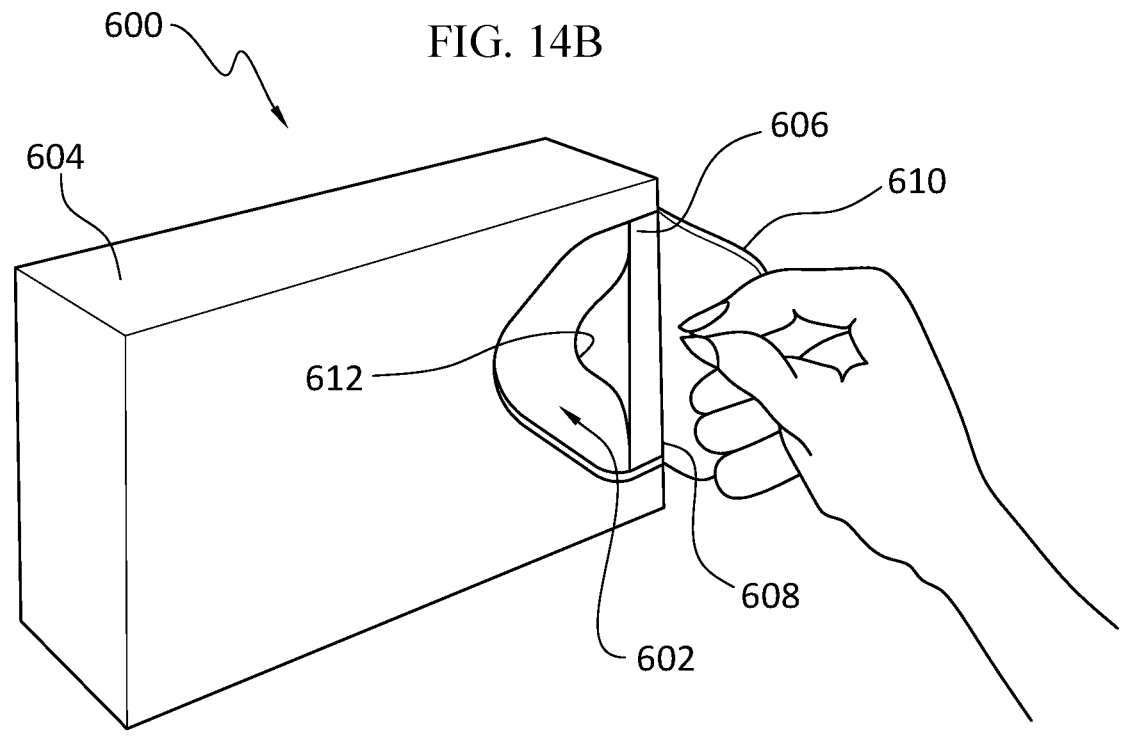

In some embodiments, the instant disclosure is directed to a medical hand covering dispensing device. Referring to FIGS. 14A and 14B, the dispensing device 600 may hold a stack 602 of a plurality of the medical hand coverings described herein. FIG. 14A illustrates one example of stack 602 of a plurality of medical hand coverings. The dispensing device may comprise a container 604 defining an interior 606 for storing the plurality of hand coverings of stack 602 and an aperture 608 through which the medical hand coverings within the container 604 may be manually removed. Dispensing device 600 may have a closure member or structure 610 (e.g., flap, lip or other sealing or closing structure) which can be readily attached to and removed from a body of container 604 to close/seal or expose aperture 608. As seen in FIG. 14B, closure member 610 is in an open position exposing aperture 608 to allow an individual to remove medical hand coverings from container 604 through aperture 608. Referring to FIGS. 14A and 14B, a surface or face of one, two or all of the medical hand coverings in stack 602 may have a waved cut-away, notch or groove 612 to allow for easy opening. Member 612 may be formed in any suitable surface or face including the surface of the medical hand covering corresponding to a dorsal side of a hand or the surface of the medical hand covering corresponding to a palm side of a hand. The storage or operating orientation of device 600 can be readily varied from that shown in FIG. 14B to any suitable orientation including an orientation in which member 610 extends horizontally and forms an upper or uppermost surface of device 600. Member 610 in FIG. 14B is shown extending vertically and forming a right side of device 600.

The container may have a foot print that corresponds to the foot print of the medical hand covering packaged therein. For instance, for a medical hand covering having a width ranging from about 100 mm to about 150 mm and a length ranging from about 100 mm to about 600 mm, the container may have a foot print ranging from about 100 mm×100 mm to about 150 mm×600 mm; for a medical hand covering having a width ranging from about 110 mm to about 120 mm and a length ranging from about 220 mm to about 240 mm, the container may have a foot print ranging from about 110 mm×220 mm to about 120 mm×240 mm. Suitable container foot prints may be derived similarly for other medical hand coverings having any of the width and length combinations disclosed herein.

The depth if the container may vary depending, for instance, on the number of medical hand coverings packaged therein. In certain embodiments, the depth of the container may range from about 50 mm to about 100 mm, from about 55 mm to about 95 mm, from about 60 mm to about 85 mm, or from about 65 mm to about 75 mm.

In certain embodiments, the foot print and depth of the packaging container is similar to that of containers that are currently used in the market for ease of use. For example, the container may be a cardboard box with loosely filled medical hand coverings, a pouch with a stacked plurality of medical hand coverings, a single-use sealed pouch with a sterile medical hand covering, a multi-use plastic container filled with medical hand coverings. The single-use sealed pouch may be a portable container design for on-the-go examinations.

The medical hand coverings may be packaged in the dispensing device in various configurations, such as, without limitations, stacked one on top of another, connected in a daisy chain configuration, loosely filled, or a combination thereof.

In one embodiment, the stack of medical hand coverings are stored in the interior of the container such that a surface of the medical hand covering corresponding to a dorsal side of a hand enclosed by the medical hand covering faces outwards of the container. In this embodiment, a method of dispensing a medical hand covering from the dispensing device may comprise removing a medical hand covering from the container (through the aperture) via a surface of the medical hand covering corresponding to a dorsal side of a hand enclosed by the medical hand covering.

In another embodiment, the stack of medical hand coverings are stored in the interior of the container such that the one end of the medical hand covering closer to the opening faces outwards of the container. In this embodiment, a method of dispensing a medical hand covering from the dispensing device may comprise removing a medical hand covering from the container (through the aperture) via a surface closer to the opening of the medical hand covering.

The dispensing methods described herein aim at improved logistics, hygienic and smart dispensing which maintains the sterility of a surface of the medical hand covering that would be in contact and/or in closest proximity to a patient upon examination (e.g., a surface of the medical hand covering corresponding to a palm side of a hand enclosed by the medical hand covering).

Industrial Applications

In one embodiment, the instant disclosure is directed to a method for protecting a patient from transmission of infectious agents. The method may comprise holding a medical instrument in a hand. The method may further comprise inserting the hand holding the medical instrument into any of the medical hand coverings described herein. In certain embodiments, the hand may be first inserted into the medical hand covering (without holding a medical instrument) and the medical instrument may inserted thereafter into the medical hand covering to be held in the inner cavity of the medical hand covering by the hand. In these embodiments, it may be contemplated that less infectious agents are transmitted to a surface contacted with the hand holding the medical instrument enclosed in the medical hand covering as compared to a surface contacted with the hand holding the medical instrument without being enclosed in the medical hand covering.

In one embodiment, the instant disclosure is directed to a method of reducing anxiety in a patient upon examination with a medical instrument. The method may comprise examining the patient with any of the medical hand coverings described herein, that include a printed character thereon (as shown in FIG. 3 for example), enclosing a hand holding the medical instrument. In these embodiments, it may be contemplated that a patient examined with the hand holding the medical instrument enclosed in the medical hand covering experiences less anxiety as compared to a patient examined with a hand holding the medical instrument without being enclosed in the medical hand covering.

In certain embodiments, the instant disclosure is directed to a kit comprising one or more of any of the medical hand covering dispensing devices described herein, any of the medical hand coverings described herein (optionally enclosed in the dispensing device), and a medical instrument (such as a stethoscope).

EXAMPLES

The following examples are set forth to assist in understanding the invention and should not be construed as specifically limiting the invention described and claimed herein. Such variations of the invention, including the substitution of any or all equivalents now known or later developed, which would be within the purview of those skilled in the art, and changes in formulation or minor changes in therapeutic design, are to be considered to fall within the scope of the invention incorporated herein.

Figure 6:
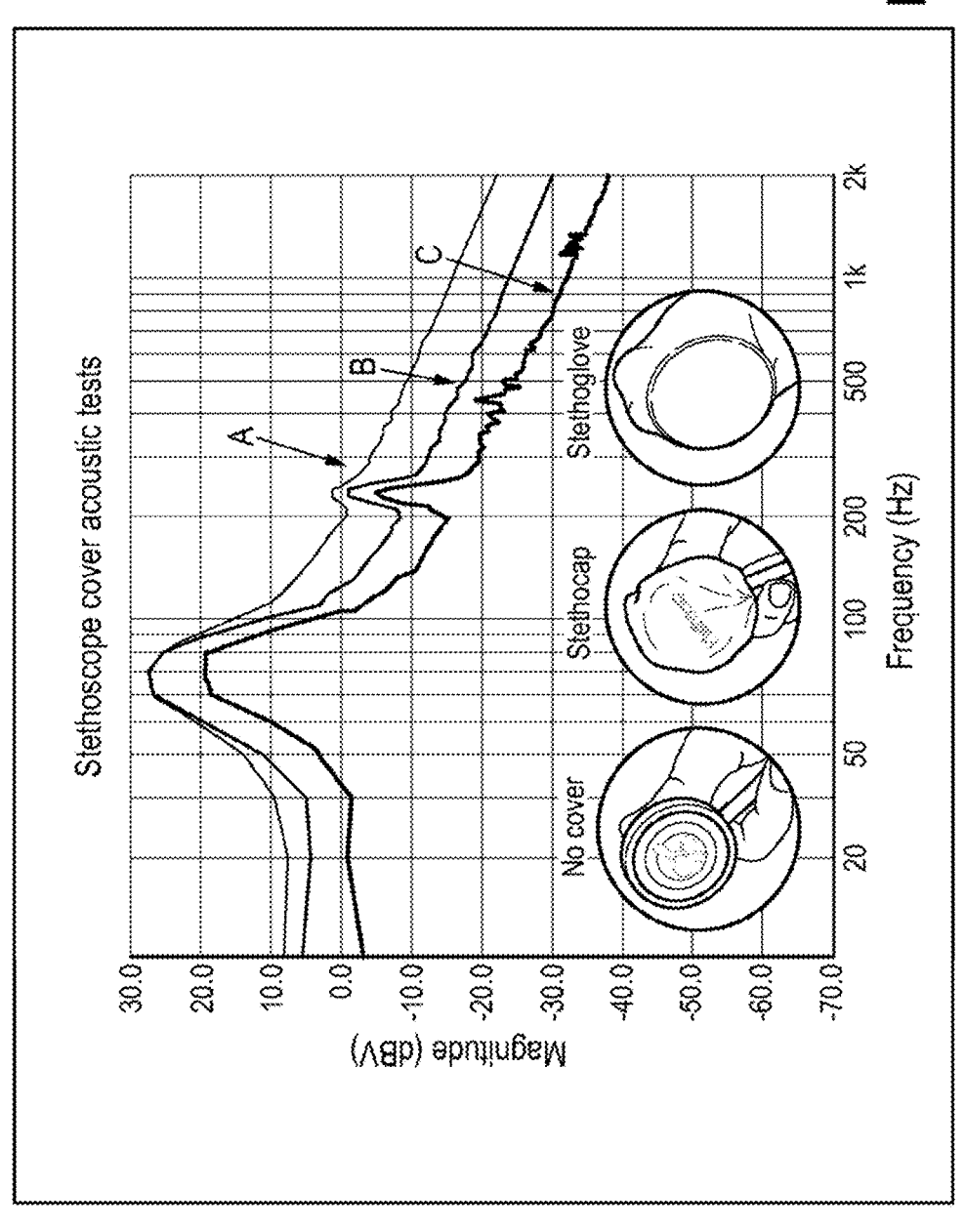
FIG. 6 depicts the acoustic performance of a stethoscope enclosed with a medical hand covering according to an embodiment as compared to a bare stethoscope and to a stethoscope enclosed with an existing commercial product.

The acoustic quality of a stethoscope used with a medical hand covering according to an embodiment was tested. The transmission of heart sounds from the Michigan University medical library was tested with: A) a Littmann stethoscope, B) a stethoscope enclosed in a medical hand covering according to an embodiment, and C) a stethoscope enclosed in a cover marketed as providing hygienic protection. The acoustic performance of the stethoscope by itself (A) as compared to the stethoscope enclosed in a cover according to an embodiment (B) and as compared to a stethoscope enclosed in an existing commercial product (C) are depicted in FIG. 6. As seen in FIG. 6, the sound curves of a bare stethoscope (A) as compared to a stethoscope enclosed in a medical hand covering described herein (B), in the medically important frequency range of about 50 Hz to about 2 kHz (or of about 50 Hz to about 100 Hz), are nearly completely superimposed. "Nearly completely superimposed" means that there is less than about 30% decibel reduction, less than about 25% decibel reduction, less than about 20% decibel reduction, less than about 15% decibel reduction, less than about 10% decibel reduction, less than about 8% decibel reduction, less than about 5% decibel reduction, less than about 3% decibel reduction, less than about 1% decibel reduction, less than about 0.5% decibel reduction, substantially no decibel reduction, or no decibel reduction (i.e., 0%), based on the decibel value of the bare stethoscope (A) at a given frequency value or frequency range. In contrast, FIG. 6 shows that the decibel level sound curves of a stethoscope enclosed in a prior art cover (stethocap) marketed as providing hygienic protection (C) compared to the bare stethoscope (A), are reduced at the medically important frequency range. The medical hand covering described herein does not alter sound transduction in the medically or diagnostically important frequency range.

Figure 7A:
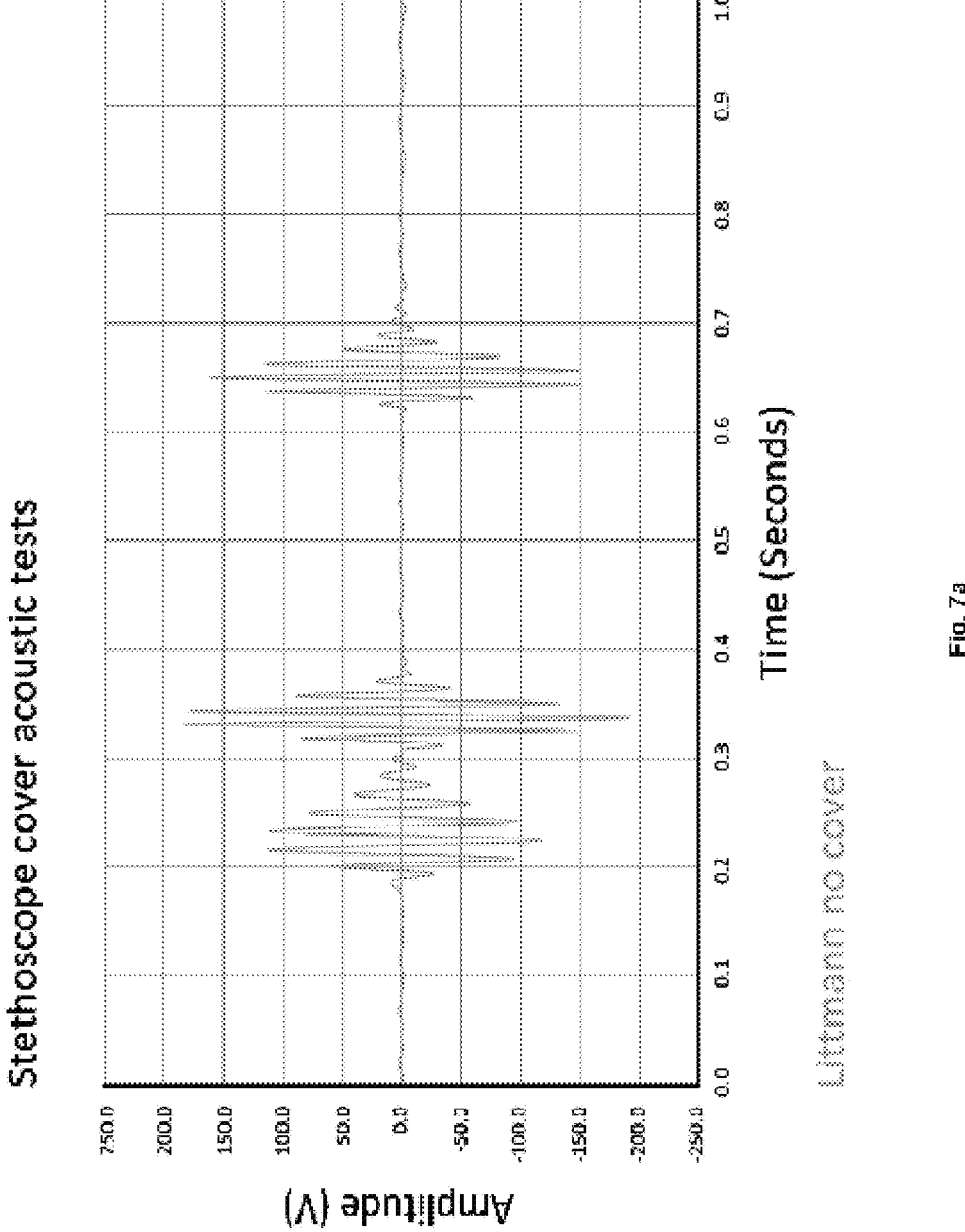
FIG. 7A depicts a waveform for a sound transmitted through a bare stethoscope.
Figure 7B:
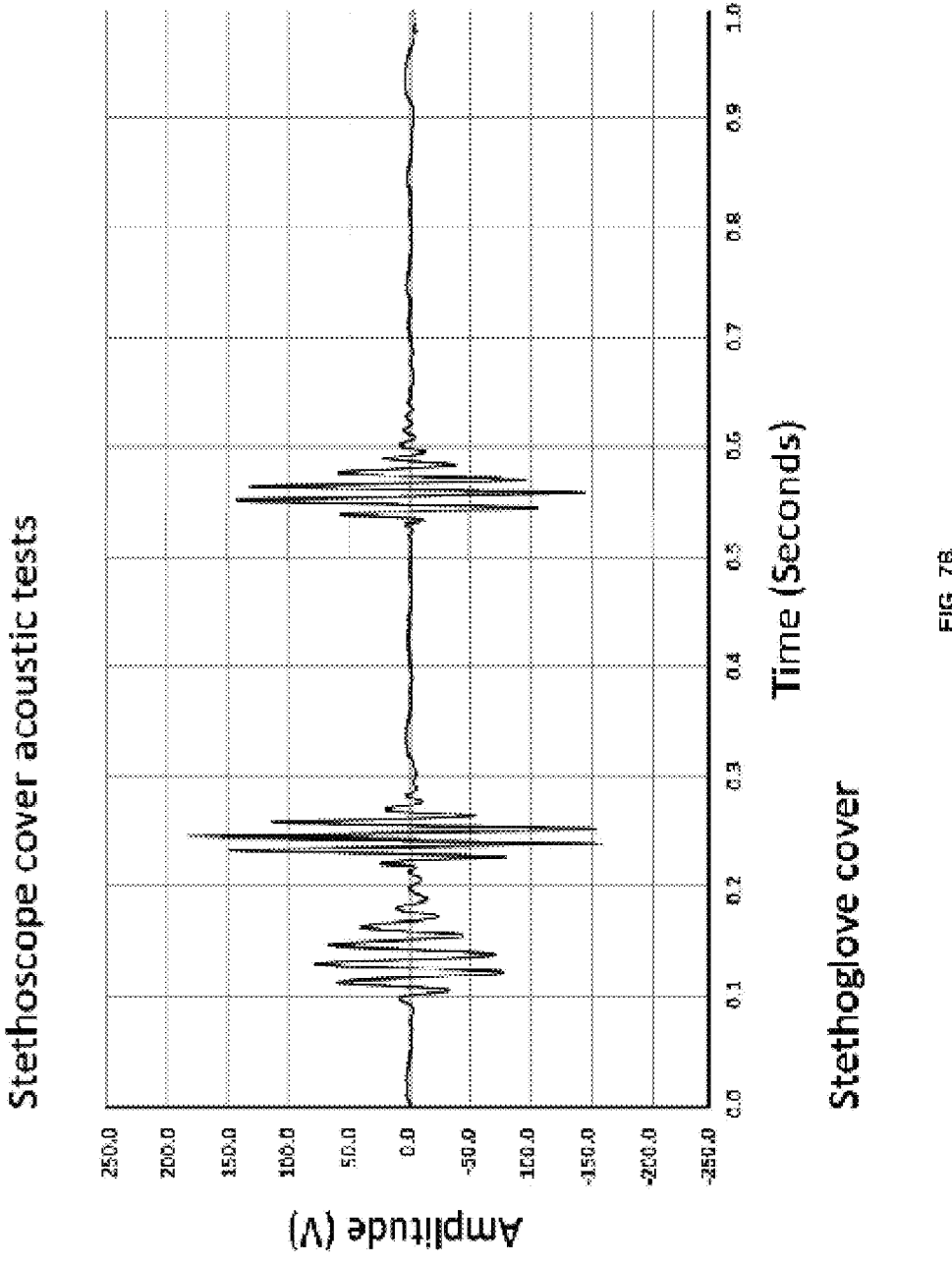
FIG. 7B depicts a waveform for a sound transmitted through a stethoscope enclosed in a medical hand covering according to an embodiment.
Figure 7C:
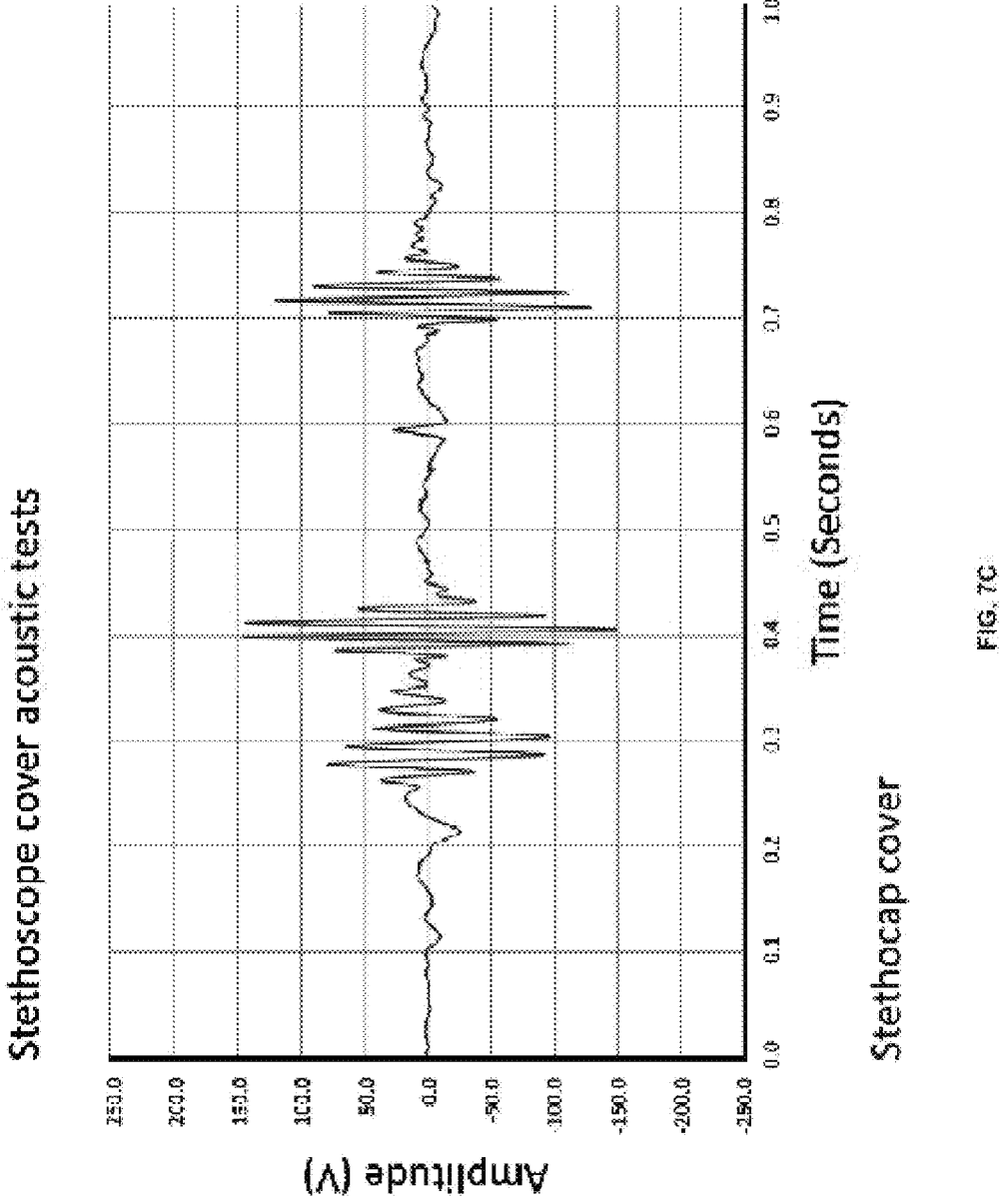
FIG. 7C depicts a waveform for a sound transmitted through a stethoscope enclosed in an existing commercial stethoscope cover.
Figure 8A:
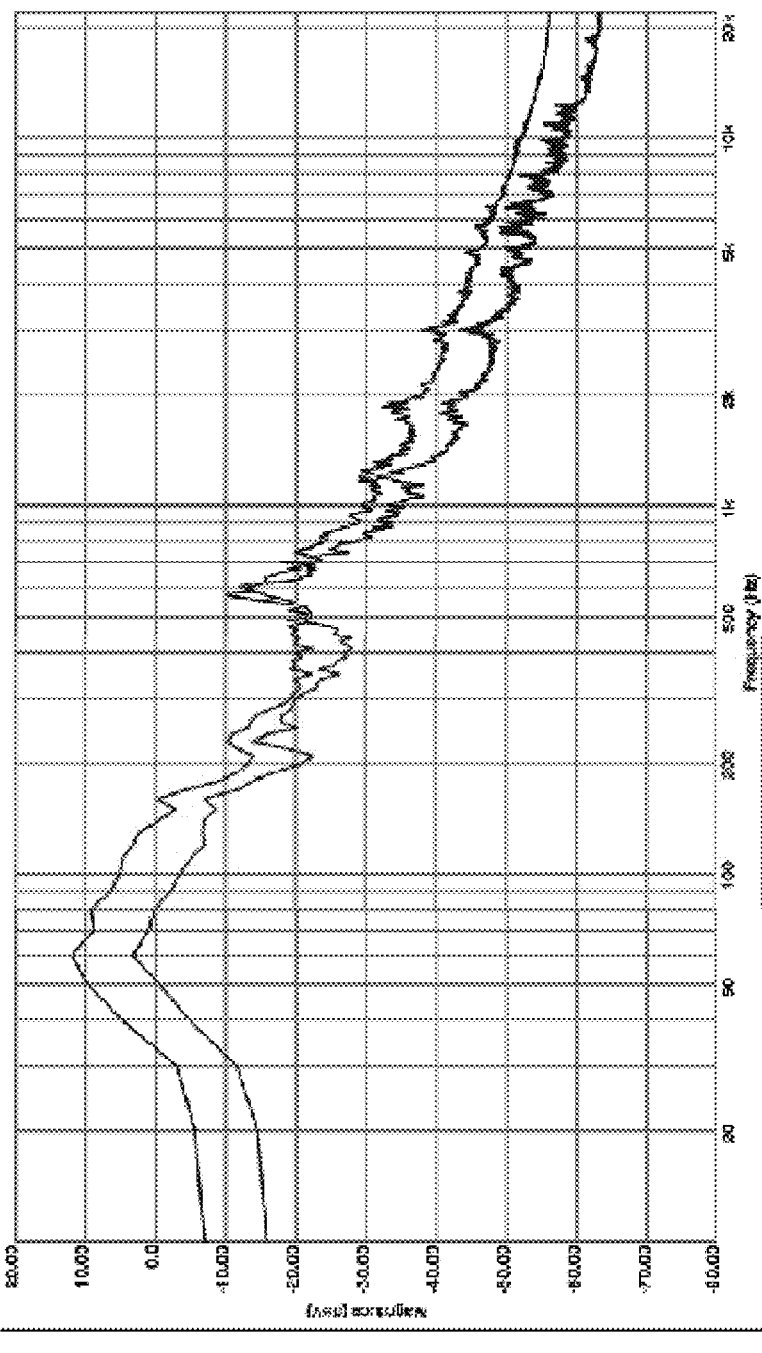
FIGS. 8A-8E show the test results of the testing of 5 different materials covering a stethoscope head versus a control testing using no covering material to show an acoustic accuracy intended to understand the reduction of quality of auscultation sounds using frequency analysis versus a standard library of heart and lung sounds, here the 3M Littmann auscultation sounds library.
Figure 8B:
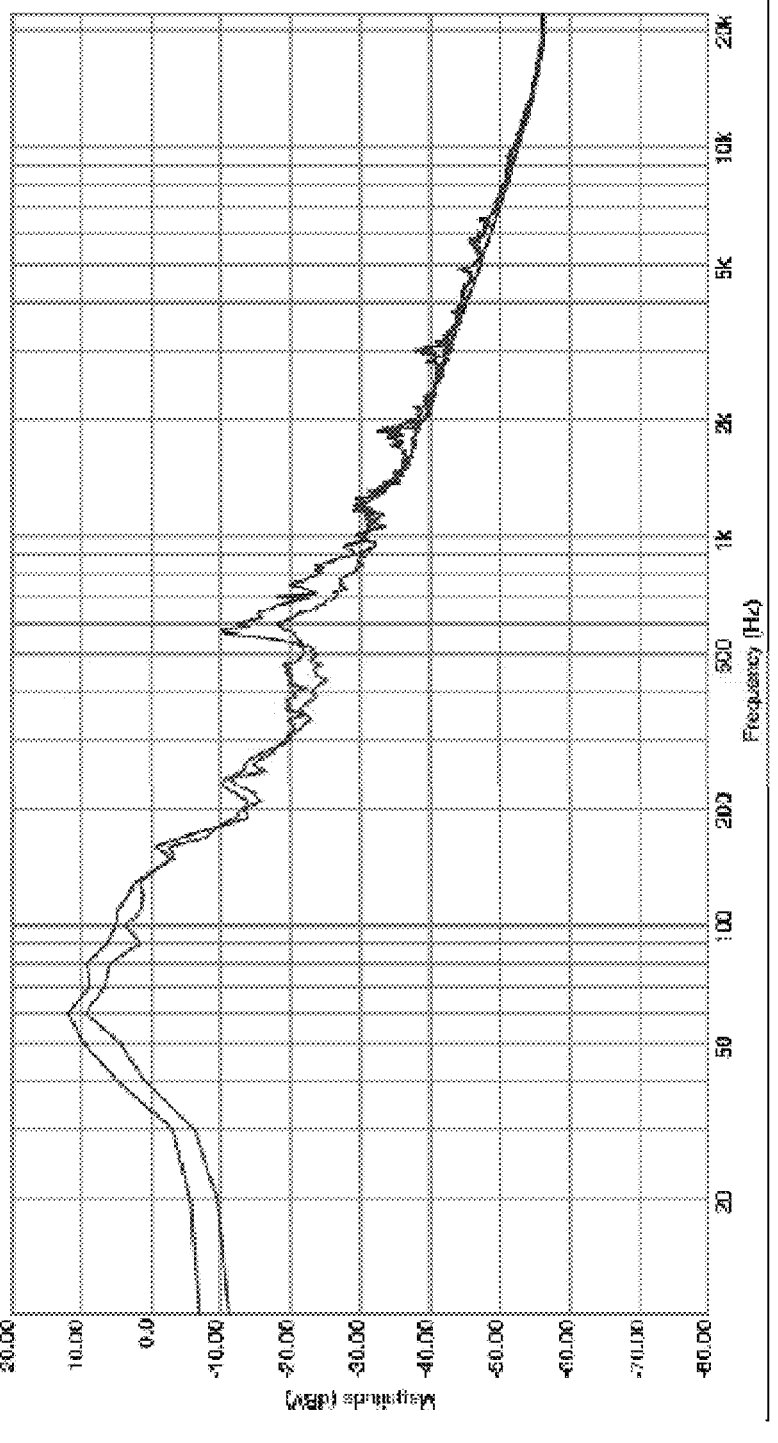
Figure 8C:
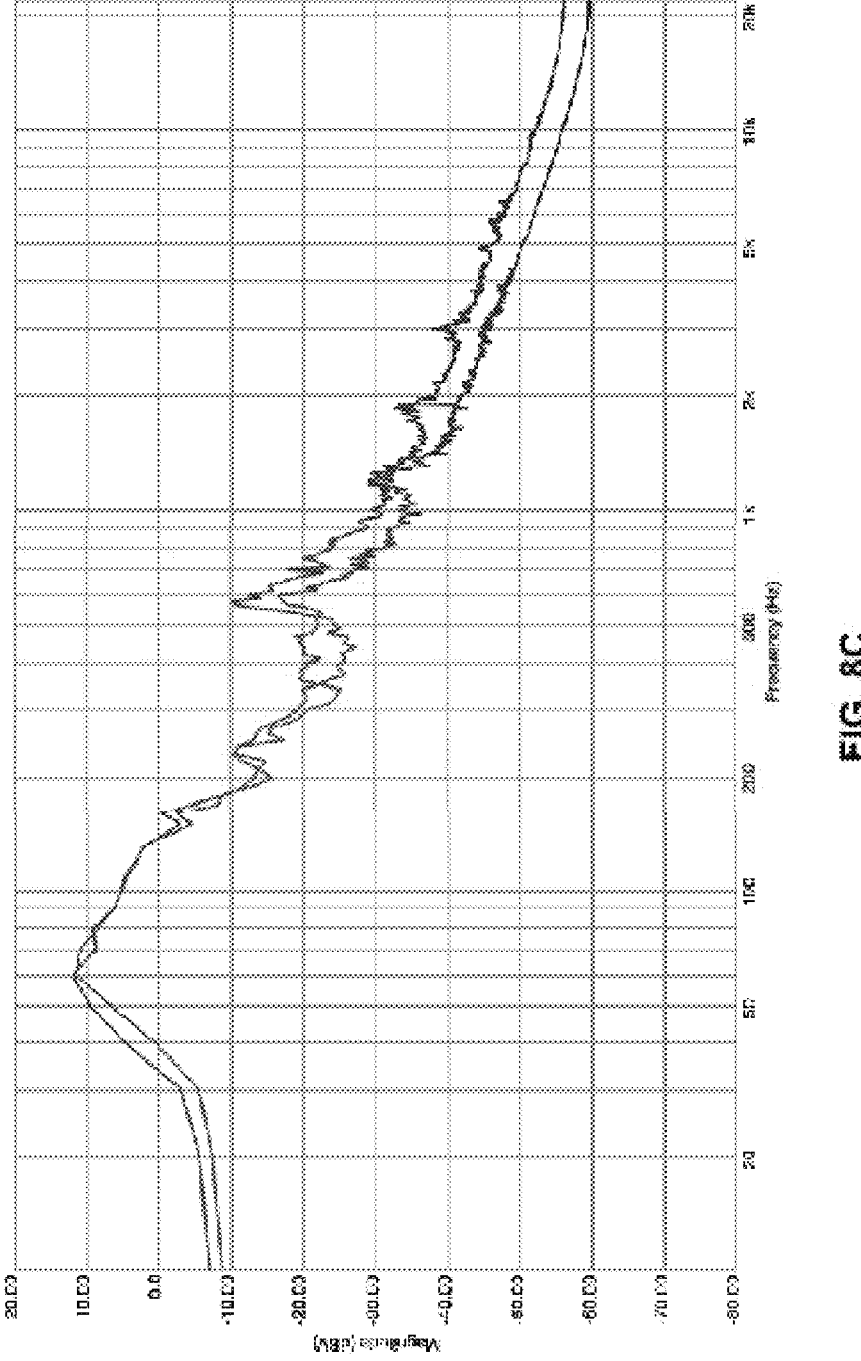
Figure 8D:
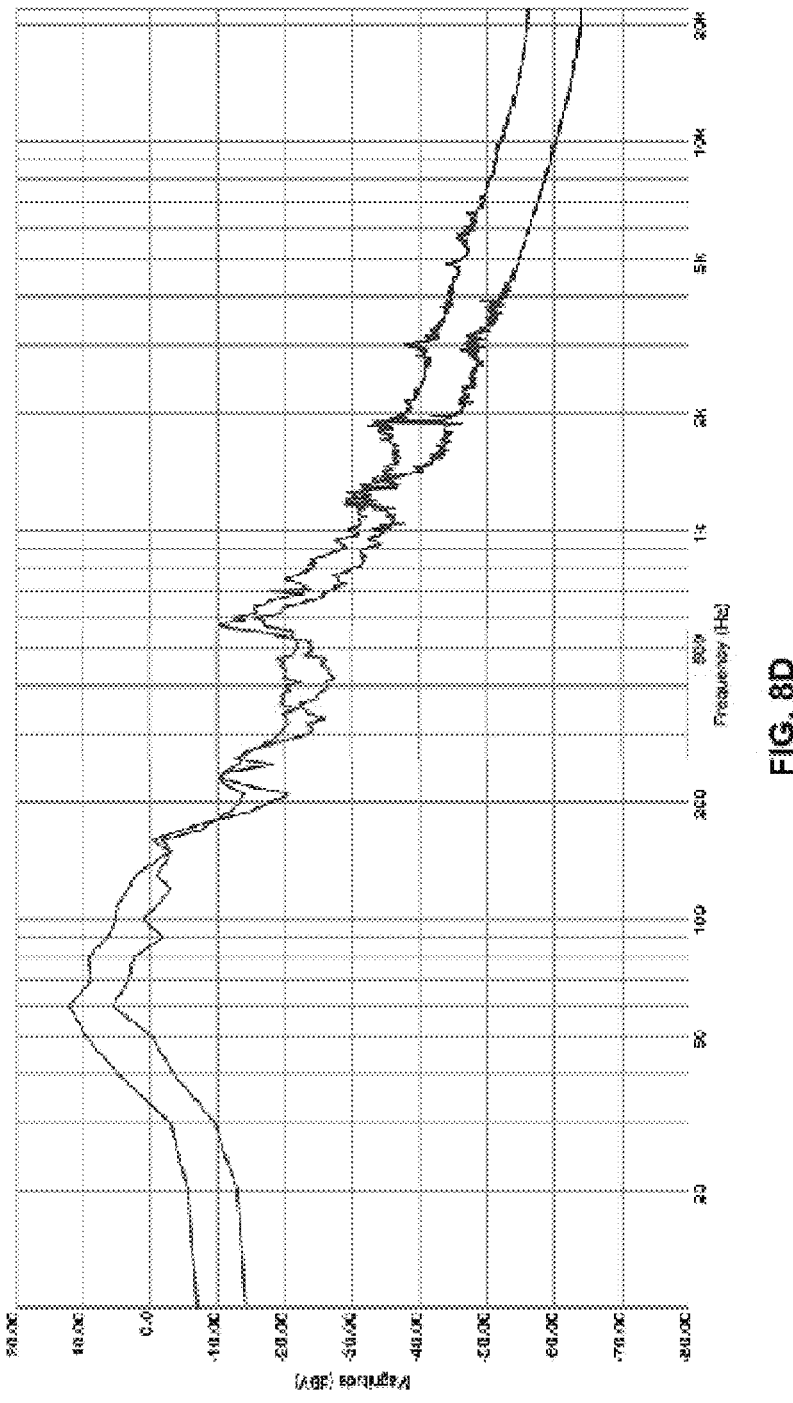
Figure 8E:
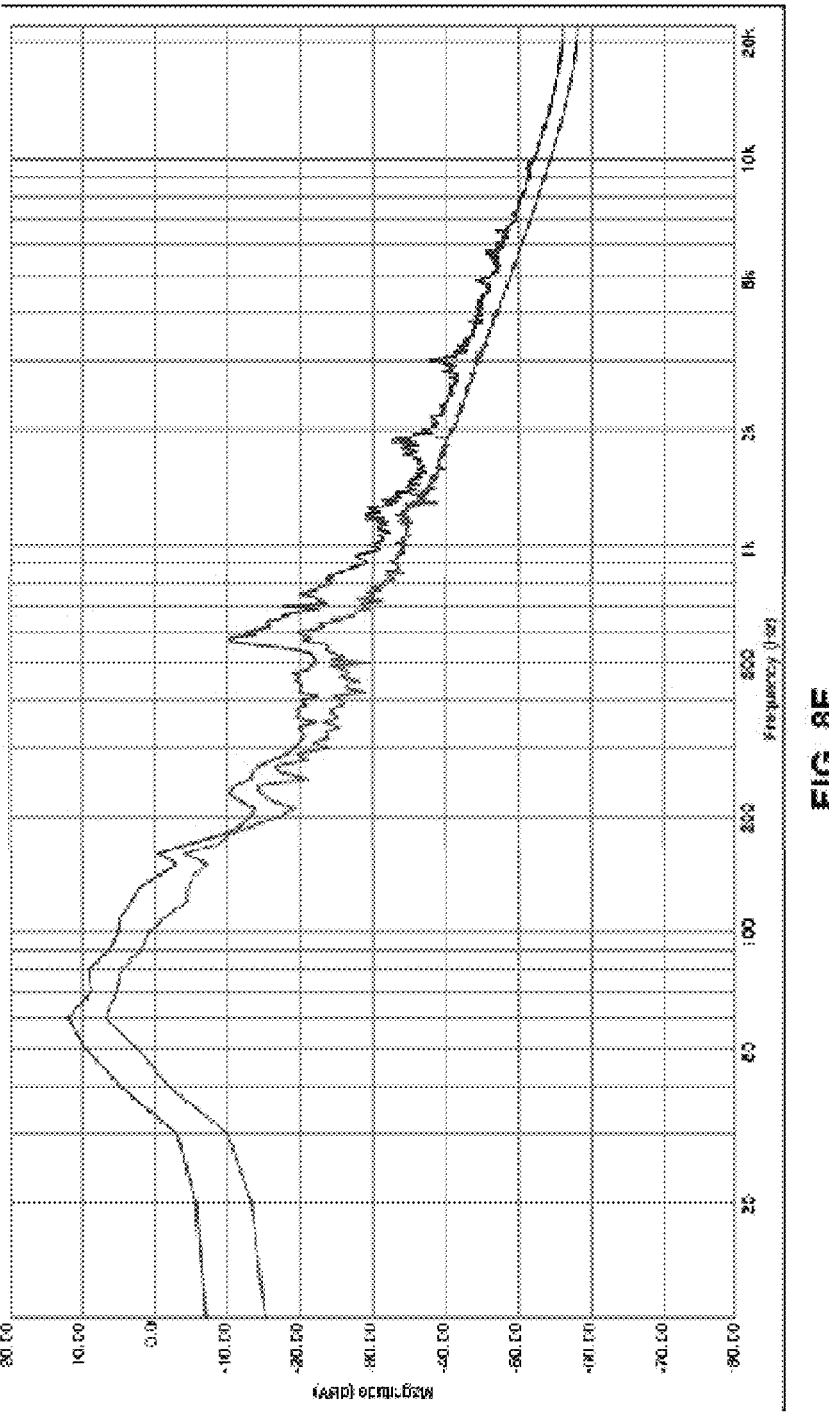
Figure 9:
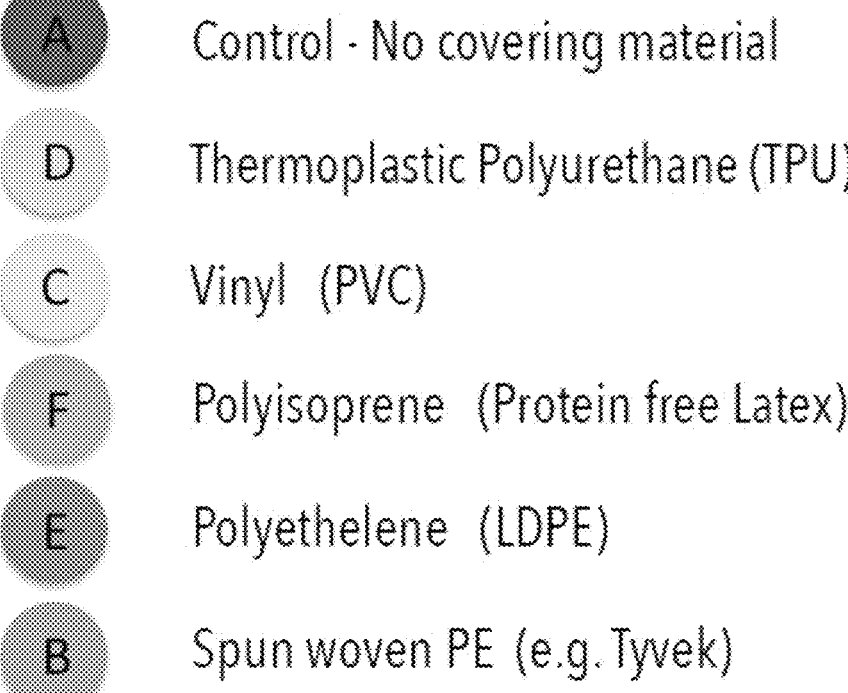
FIG. 9 depicts the sound quality summary in order of performance, the selection being based upon a qualitative assessment of accuracy as shown by the testings of FIGS. 8A-8E.
Figure 10A:
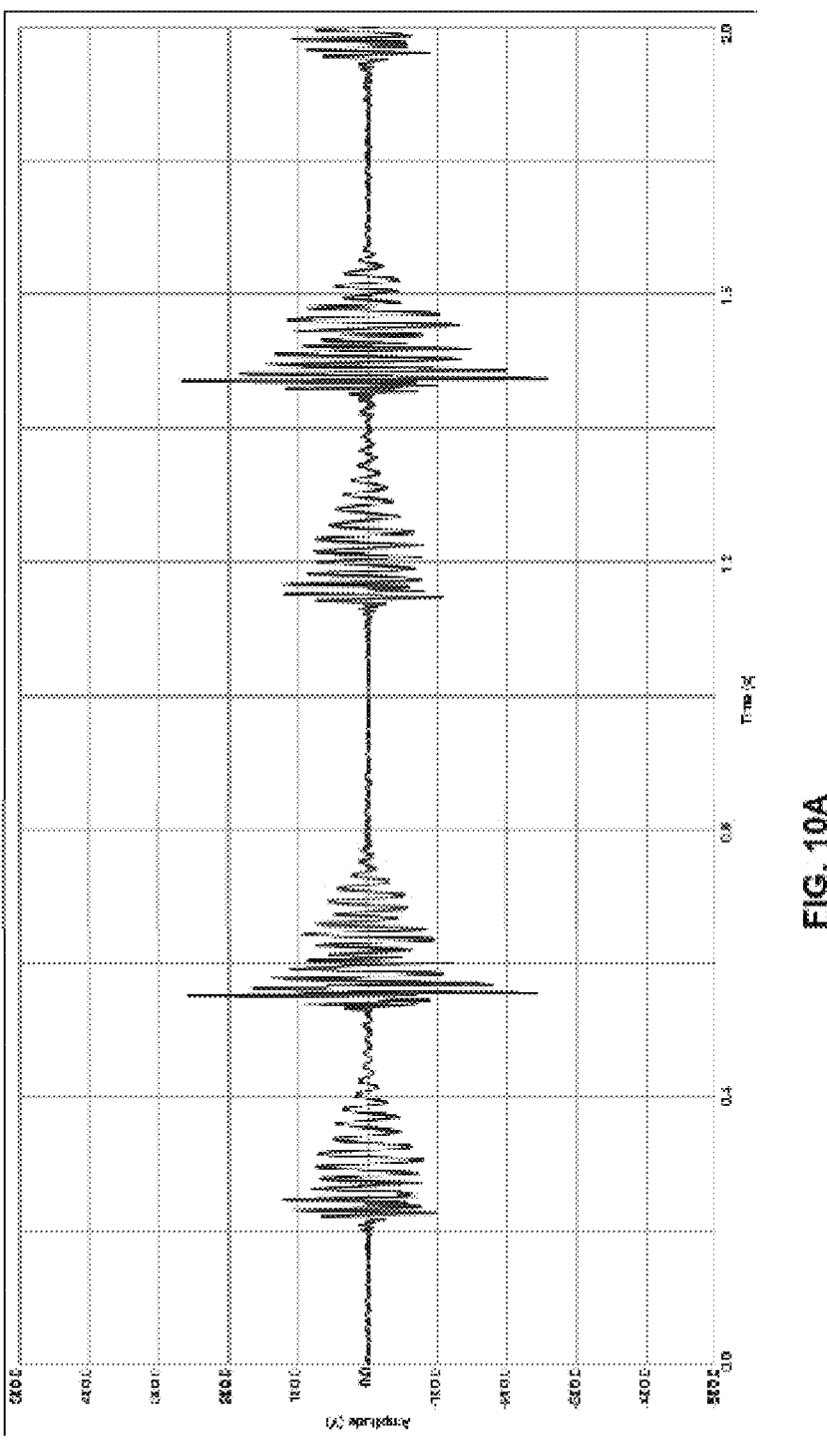
FIGS. 10A-10F show the test results of the testings of no material and five different materials covering a stethoscope head versus the afore-mentioned control testing using no covering material, the test results showing an acoustic amplitude intended to understand the reduction of sound volume using various test materials versus no material covering of a stethoscope head and by using two sound sources, a first heart sound being the sound of a normal heart, and a second sound source being the heart sound of a heart with severe aortic stenosis, both heart sounds taken from the 3M Littmann auscultation sounds library.
Figure 10B:
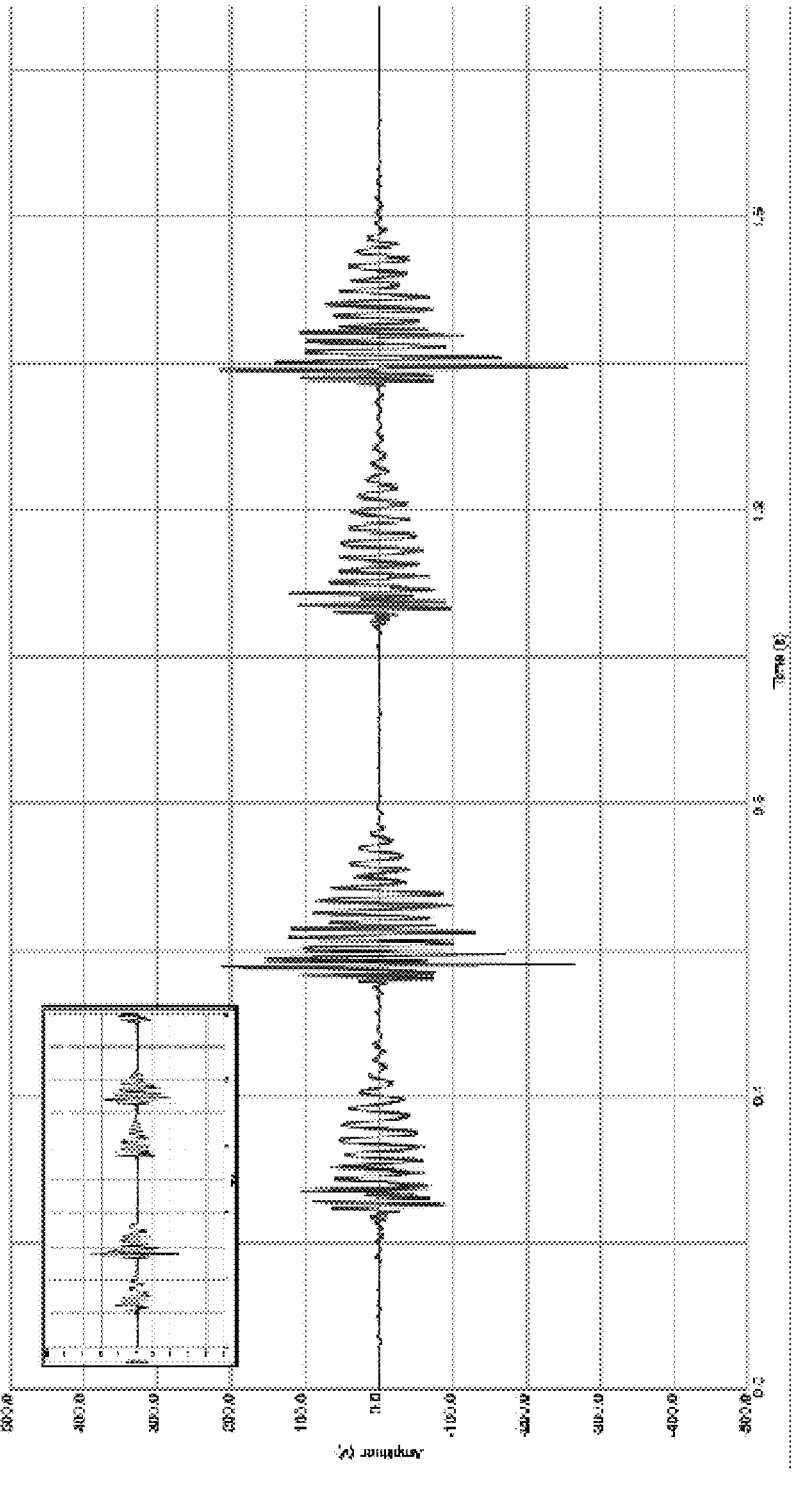
Figure 10C:
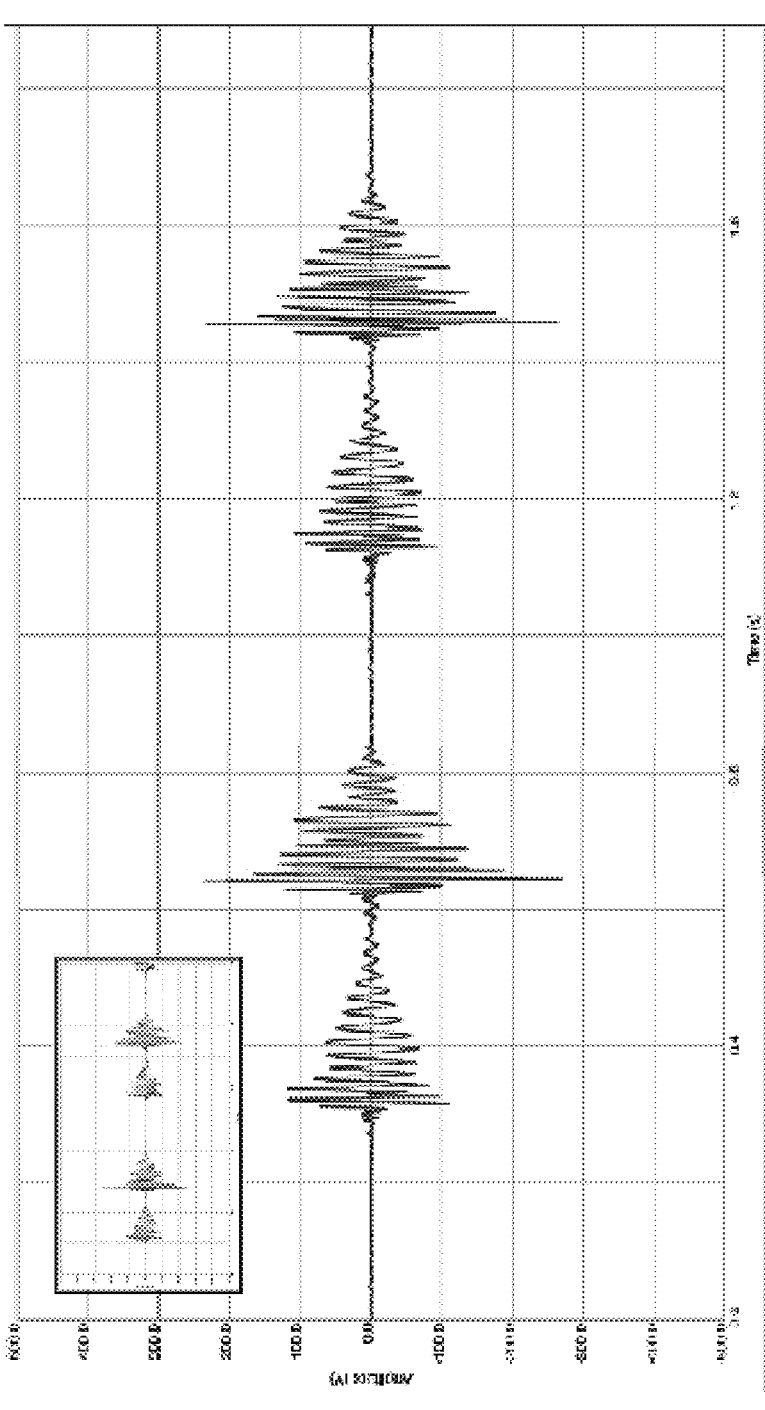
Figure 10D:
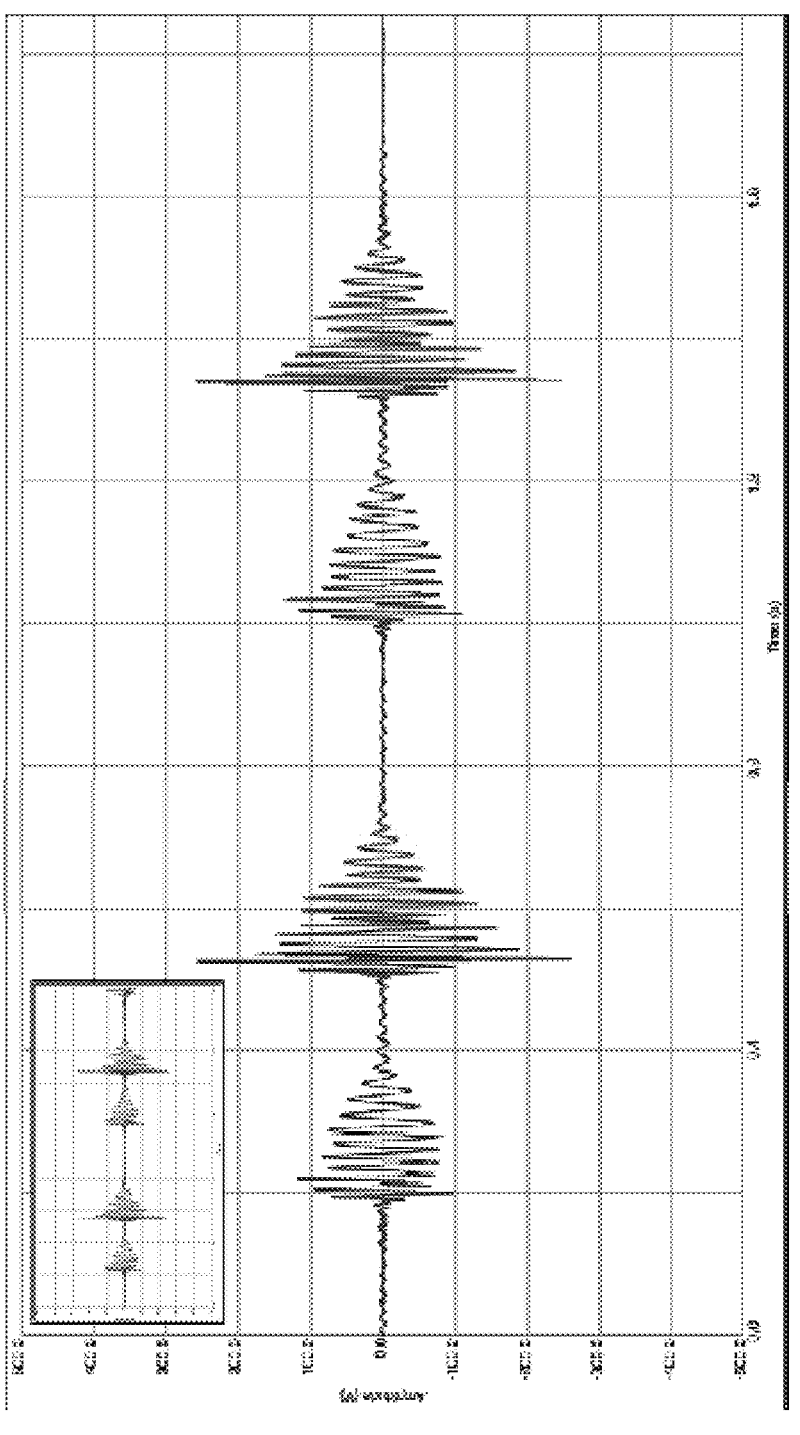
Figure 10E:
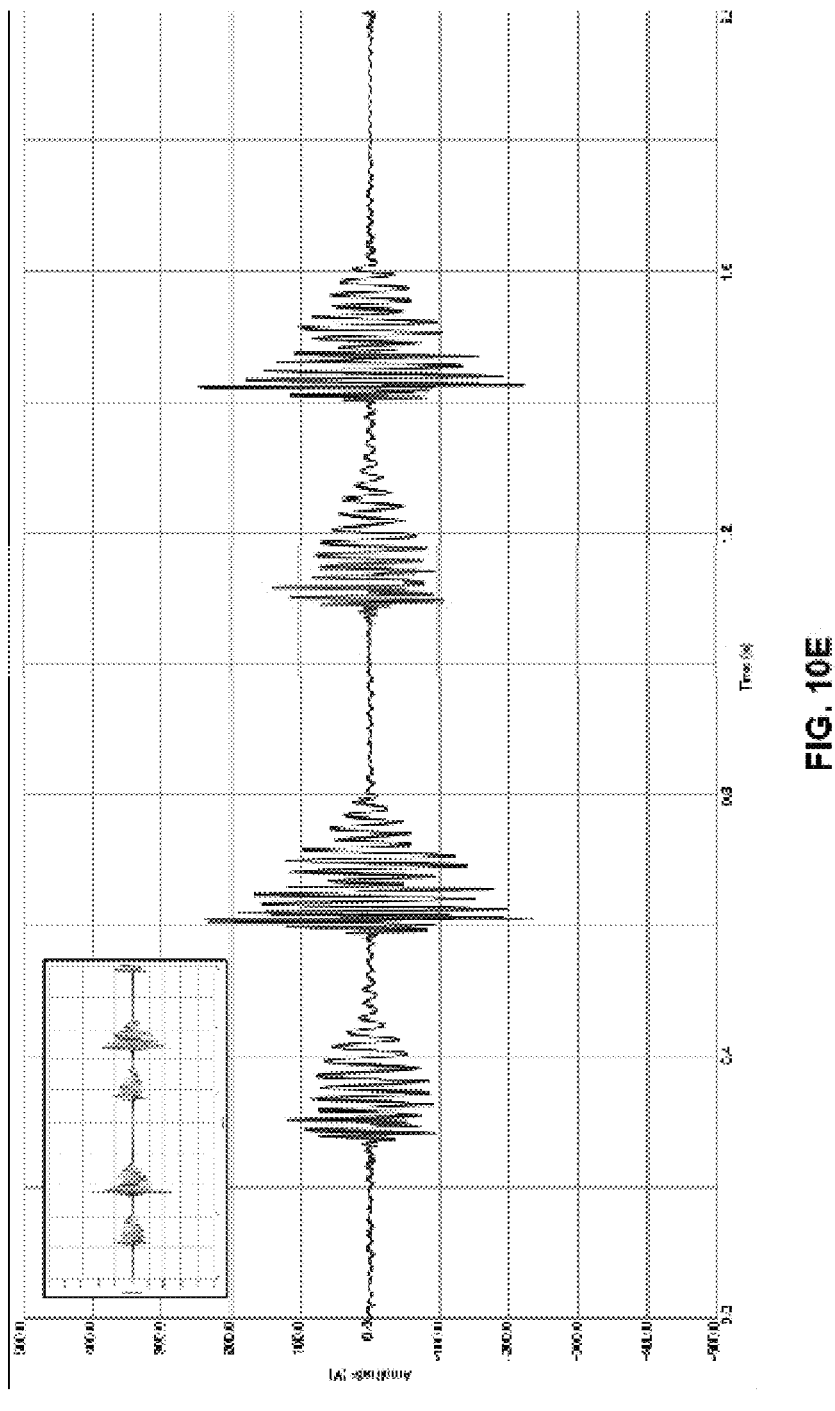
Figure 10F:
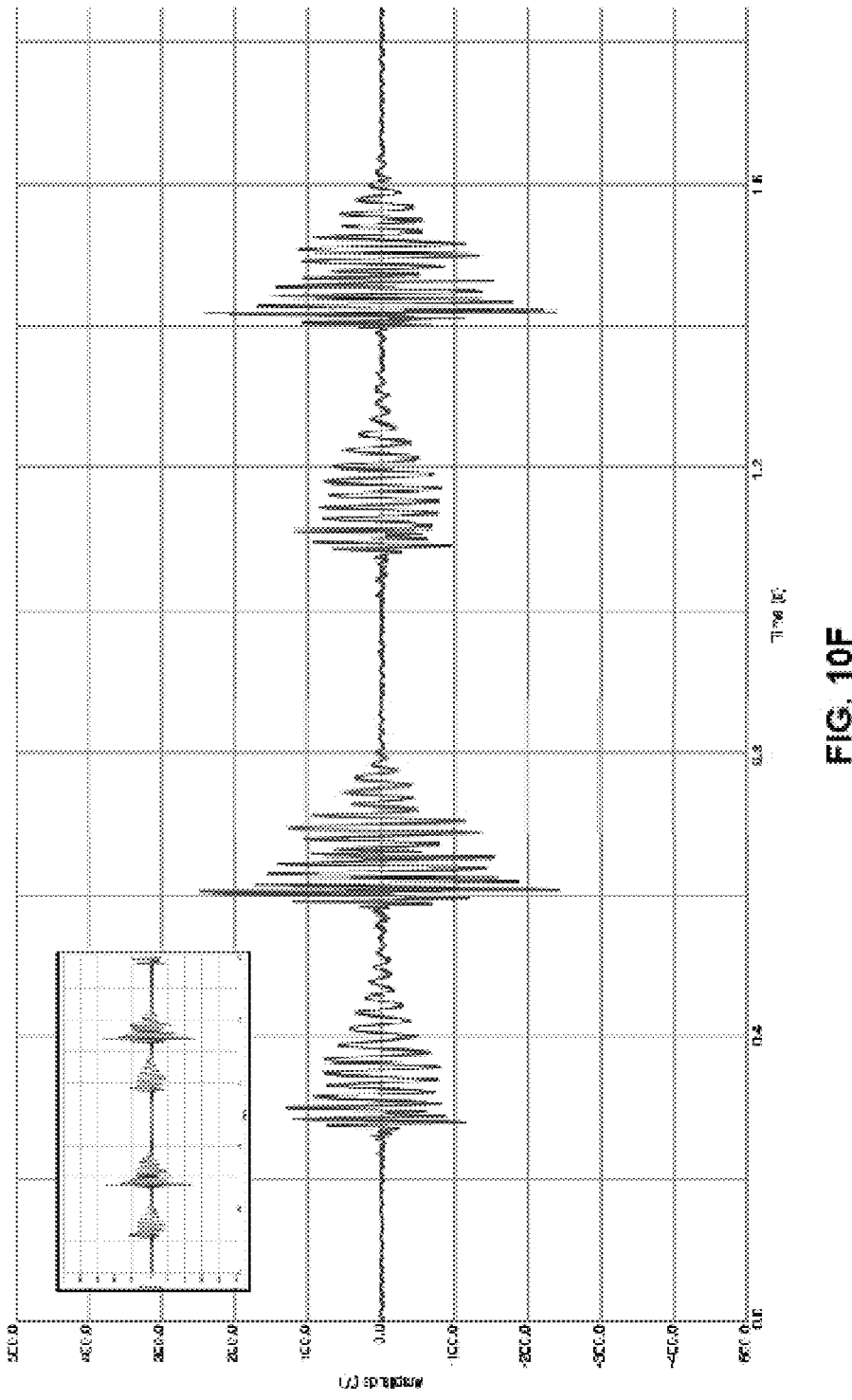
Figure 11:
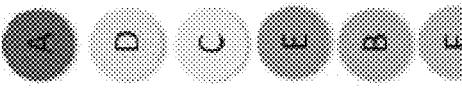
FIG. 11 shows the summary of the results of the testings shown in FIGS. 10A-10F using source 1, i.e., the normal heart sounds.

The amplitude of samples A, B, and C are depicted in FIGS. 7A, 7B, and 7C, respectively. As seen in FIGS. 7A and 7B, a stethoscope enclosed in a cover according to an embodiment (sample B) does not discernably alter the control (i.e., the acoustic performance of the stethoscope by itself—sample A). In contrast, the existing commercial product (stethocap—made of rigid, semirigid, or porous material) enclosing a stethoscope (sample C) does introduce crackles with normal finger pressure. The sound pollution detected with the product tested in sample C is visible in the waveform shown in FIG. 7C. Such sound pollution may lead to misdiagnosis. FIGS. 8A-8E show the test results of the testing of 5 different materials covering a stethoscope head versus a control testing using no covering material to show an acoustic accuracy intended to understand the reduction of quality of auscultation sounds using frequency analysis versus a standard library of heart and lung sounds, here the 3M Littmann auscultation sounds library. FIG. 8A shows a control testing without covering material (upper curve) and a testing with spun woven polyethylene as covering material covering the stethoscope (lower curve). FIG. 8B shows a control testing without covering material (upper curve) and a testing with vinyl (PVC) in the lower curve. FIG. 8C shows a control testing without covering material (upper curve) and a testing of thermoplastic polyurethane (TPU) (lower curve). FIG. 8D shows a control testing without covering material (upper curve) and a testing of polyethylene (LDPE) as the covering material for the stethoscope (lower curve). FIG. 8E shows a control testing without covering material for the stethoscope (upper curve) and a testing of polyisoprene (protein free latex) as a covering material for covering the stethoscope in the lower curve. FIG. 9 depicts the sound quality summary in order of performance, the selection being based upon a qualitative assessment of accuracy as shown by the testings of FIGS. 8A-8E. FIGS. 10A-10F show the test results of the testings of no material covering the stethoscope, FIG. 10A, and with five different materials covering a stethoscope head versus the afore-mentioned control testing using no covering material, the test results showing an acoustic amplitude intended to understand the reduction of sound volume using various test materials versus no material covering of a stethoscope head and by using two sound sources, a first heart sound source being the sound of a normal heart, and a second heart sound source being the heart sound of a heart with severe aortic stenosis, both heart sounds taken from the 3M Littmann auscultation sounds library. FIG. 10A shows a control amplitude of no covering material for the stethoscope. FIG. 10B shows in the left upper corner the control amplitude and in the main diagram the amplitude when using a spun woven polyethylene (e.g. Tyvek) as a covering material for the stethoscope. FIG. 10C shows in the left upper corner the control amplitude without covering material and in the main diagram the amplitude when using vinyl (PVC) as the covering material for the stethoscope. FIG. 10D shows in the left upper corner the control amplitude when using no material for covering the stethoscope and in the main diagram the resulting amplitude of the testing with thermoplastic polyurethane (TPU) as a covering material for the stethoscope. FIG. 10E shows in the left upper corner the control amplitude for the testing without covering material and in main diagram the amplitude when testing with a covering material being polyethylene for covering the stethoscope. FIG. 10F shows in the left upper corner the control amplitude for a testing without covering material and in the main diagram the resulting amplitude when covering the stethoscope with a thermosetting polyisoprene. FIG. 11 shows the summary of the results of the testings shown in FIGS. 10A-10F using source 1, i.e., the normal heart sounds. FIG. 12 shows the summary of the testings of FIGS. 10A-10F using source 2, i.e. the heart sound of a heart with severe arortic stenosis. FIG. 13 shows the test equipment used for all testings shown in FIGS. 8-12. From the tests shown and described in FIGS. 8-13 the present invention could confirm that the most preferred material for the one or more materials is an elastic thermoplastic polyurethane film (TPU). The afore-mentioned testings as shown and described with respect to FIGS. 8-13 show that the TPU material retains the audible diagnostic information more accurately than the other tested materials and also ensures that there is very little loss of volume. In noisy environments, this can be of critical advantage. Additionally, the soft elastic surface of TPU provides a non-abrasive contact with the body. When testing less flexible materials like PE, a positioning movement may possibly introduce crackles, which are a symptom of heart or lung issues and could lead to a miss-diagnosis. The TPU performed considerably better when using the softer, quitter, more complex sounds as per the severe aortics stenosis example of source 2.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is simply intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

I claim:

1. A method for protecting a patient from transmission of infectious agents comprising:

grasping a stethoscope with fingers of an adult hand;

then inserting the adult hand grasping the stethoscope into a fingerless medical hand covering, the medical hand covering tightly sealing the hand and stethoscope while allowing movement without generating disruptive sounds;

wherein the medical hand covering comprises (A) or (B), wherein (A) comprises:

a first surface corresponding to a palm side of the adult hand;

a second surface corresponding to a dorsal side of the adult hand;

the first surface and the second surface defining an inner cavity tightly enclosing the stethoscope and the adult hand grasping said stethoscope; and an opening on one end of the covering adapted to allow entry of the adult hand and the stethoscope into the inner cavity, and an opposite end of the covering being closed to prevent transmission of the infectious agents while using the stethoscope; and;

an hourglass shape characterized by a wider width in a first portion of the inner cavity that is to enclose the adult hand grasping the stethoscope, a narrower width between said first portion and a second portion of the inner cavity at the one end of the medical hand covering where the opening is, said second portion having a wider width than the narrower width;

the medical hand covering has a cross-section that is round or oval, an unstretched circumference around the medical hand covering when measured across a side of a palm or to a thumb of the adult hand ranges from about 200 mm to about 260 mm, and when the medical hand covering lays flat, each face having a width ranging from about 100 mm to about 150 mm; and, wherein "about" includes the recited number plus/minus 10%; and wherein (B) comprises:

one or more materials defining an inner cavity tightly enclosing the stethoscope and the adult hand grasping said stethoscope; and an opening on one end of the covering adapted to allow entry of the adult hand and the stethoscope into the inner cavity, and an opposite end of the covering being closed to prevent transmission of the infectious agents while using the stethoscope, and;

an hourglass shape characterized by a wider width in a first portion of the inner cavity that is to enclose the adult hand grasping the stethoscope, a narrower width between said first portion and a second portion of the inner cavity at the one end of the medical hand covering where the opening is, said second portion having a wider width than the narrower width; and the medical hand covering has a cross-section that is round or oval, an unstretched circumference around the medical hand covering when measured across a side of a palm or to a thumb of the adult hand ranges from about 200 mm to about 260 mm, and when the medical hand covering lays flat, each face having a width ranging from about 100 mm to about 150 mm; and, wherein "about" includes the recited number plus/minus 10%.

2. The method of claim 1, wherein less infectious agents are transmitted to a surface contacted with the adult hand holding the stethoscope enclosed in the medical hand covering as the inner cavity is configured to prevent both the adult hand holding the stethoscope and the stethoscope from directly contacting the surface contacted.

3. The method of claim 2, wherein the one or more materials is acoustically transmissive with respect to an acoustic performance of the stethoscope, in that a sound curve of a bare stethoscope compared to the stethoscope enclosed in the medical hand covering are nearly completely superimposed in a frequency range of about 50 Hz to about 2 kHz, wherein nearly completely superimposed means that there is less than about 30% decibel reduction, based on a decibel value of the bare stethoscope at said frequency range, wherein about includes the recited number +10%.

4. The method according to claim 1, further including the step of providing a medical hand covering device for holding a stack of medical hand coverings and for manually dispensing medical hand coverings from said stack, the medical hand covering dispensing device comprising a container defining an interior for storing the stack of medical hand coverings and an aperture through which the medical hand coverings within the container may be removed.

5. The method of claim 4, wherein the stack of medical hand coverings are stored in the interior of the container such that the second surface of the medical hand covering faces outwards of the container.

6. The method of claim 4, wherein the stack of medical hand coverings are stored in the interior of the container such that the one end of the medical hand covering closer to the opening faces outwards of the container.

7. The method of claim 1, wherein the one or more materials, independently, comprise one or more of thermoset rubbers or thermoplastic materials.

8. The method of claim 1, wherein the one or more materials is stretchy and the unstretched circumference around the medical hand covering ranges from about 210 mm to about 250 mm, and when the medical hand covering lays flat, the width of each face ranging from about 105 mm to about 125 mm, wherein about includes the recited number +10%.

9. The method of claim 1, wherein the medical hand covering is ambidextrous.

10. The method of claim 1, wherein a sound quality obtained via the stethoscope when it is used with the medical hand covering is the same as a sound quality obtained via the stethoscope when it is used without the medical hand covering, wherein the sound quality comprising one or more of amplitude, frequency, or decibel level.

11. The method of claim 1, wherein the opening further comprises a cuff bead.

12. The method of claim 1, wherein the one or more materials are transparent or opaque.

13. The method of claim 1, wherein the inner cavity is adapted to tightly enclose the adult hand holding the stethoscope in a fisted position.

14. The method of claim 1, wherein the inner cavity is adapted to tightly enclose both the adult hand holding the stethoscope and at least a part of the stethoscope gripped by the adult hand, the part being a chestpiece of the stethoscope.

\* \* \* \* \*